(12) United States Patent
Dellovade

(10) Patent No.: US 10,716,788 B2
(45) Date of Patent: Jul. 21, 2020

(54) METHODS FOR TREATING MS USING PYRIMIDINE AND PYRIDINE COMPOUNDS WITH BTK INHIBITORY ACTIVITY

(71) Applicant: Merck Patent GmbH, Darmstadt (DE)

(72) Inventor: Tammy Dellovade, Carlisle, MA (US)

(73) Assignee: Merck Patent GmbH, Darmstadt (DE)

( * ) Notice: Subject to any disclaimer, the term of this patent is extended or adjusted under 35 U.S.C. 154(b) by 430 days.

(21) Appl. No.: 15/352,657

(22) Filed: Nov. 16, 2016

(65) Prior Publication Data
US 2017/0136018 A1    May 18, 2017

Related U.S. Application Data

(60) Provisional application No. 62/256,199, filed on Nov. 17, 2015.

(51) Int. Cl.
| | |
|---|---|
| *A61K 31/506* | (2006.01) |
| *C07D 495/04* | (2006.01) |
| *C07D 405/14* | (2006.01) |
| *C07D 403/12* | (2006.01) |
| *C07D 401/14* | (2006.01) |
| *C07D 413/12* | (2006.01) |
| *C07D 403/14* | (2006.01) |
| *A61K 45/06* | (2006.01) |
| *A61K 31/4545* | (2006.01) |
| *C07D 413/14* | (2006.01) |
| *C07D 401/04* | (2006.01) |
| *A61K 31/4418* | (2006.01) |

(Continued)

(52) U.S. Cl.
CPC .......... *A61K 31/506* (2013.01); *A61K 31/445* (2013.01); *A61K 31/4418* (2013.01); *A61K 31/455* (2013.01); *A61K 31/4545* (2013.01); *A61K 31/505* (2013.01); *A61K 31/5377* (2013.01); *A61K 31/55* (2013.01); *A61K 31/69* (2013.01); *A61K 45/06* (2013.01); *C07D 401/04* (2013.01); *C07D 401/14* (2013.01); *C07D 403/12* (2013.01); *C07D 403/14* (2013.01); *C07D 405/14* (2013.01); *C07D 413/12* (2013.01); *C07D 413/14* (2013.01); *C07D 495/04* (2013.01)

(58) Field of Classification Search
CPC .............. A61K 31/445; A61K 31/4418; A61K 31/506; A61K 31/55
USPC ........................................................ 514/256
See application file for complete search history.

(56) References Cited

U.S. PATENT DOCUMENTS 9,073,947 B2 *    7/2015  Hodous ................ C07D 213/68

FOREIGN PATENT DOCUMENTS

| WO | 1998024782 A2 | 6/1998 |
| WO | 2005095400 A1 | 10/2005 |

(Continued)

OTHER PUBLICATIONS

Hartkamp et al, International J. of Interferon, Cytokine and Mediator Research (2015), vol. 7, pp. 27-34. (Year: 2015).*

(Continued)

*Primary Examiner* — Craig D Ricci
*Assistant Examiner* — Janet L. Coppins
(74) *Attorney, Agent, or Firm* — Grüneberg and Myers PLLC

(57) ABSTRACT

The present invention provides methods of treating MS using pyrimidine and pyridine compounds which are inhibitors of Bruton's tyrosine kinase (BTK).

4 Claims, 25 Drawing Sheets

(51) Int. Cl.
*A61K 31/445* (2006.01)
*A61K 31/455* (2006.01)
*A61K 31/505* (2006.01)
*A61K 31/5377* (2006.01)
*A61K 31/55* (2006.01)
*A61K 31/69* (2006.01)

(56) References Cited

FOREIGN PATENT DOCUMENTS

| | | |
|---|---|---|
| WO | 2006136442 A1 | 12/2006 |
| WO | 2008039218 A2 | 4/2008 |
| WO | 2009055418 A1 | 4/2009 |
| WO | 2011-029804 | 3/2011 |
| WO | 2011/099764 | 8/2011 |
| WO | 2012170976 A2 | 12/2012 |
| WO | 2014011568 A1 | 1/2014 |
| WO | 2014093230 A2 | 6/2014 |
| WO | 2014163161 A1 | 10/2014 |
| WO | 2015042077 A1 | 3/2015 |

OTHER PUBLICATIONS https://www.mayoclinic.org/diseases-conditions/multiple-sclerosis/symptoms-causes/syc-20350269, Aug. 4, 2017. (Year: 2017).*
Fong et al., Recent Patents on CNS Drug Discovery, 2008, 3(3): 153-165.
Foster A.B., Advance in Drug Research, 1985, 14: 1-39.
Garcia-Bustos, et al., EMBO J., 1994,13: 2352-2361.
Gillette et al., Biochemistry, 1994, 33: 2927-2937.
Hanks, S.K., Hunter, T., Faseb J., 1995, 9: 576-596.
Hanzlik et al., J. Org. Chem., 1990, 55: 3992-3997.
Hiles, et al., Cell, 1992, 70:419-429.
Jarman et al., Carcinogenesis, 1995, 16(4): 683-688.
Knighton, et al., Science, 1991, 253:407-414.
Kunz, et al., Cell, 1993, 73:585-596.
T. Kurosaki, Curr Op Imm, 2000, 276-281.
Reider et al., J. Org. Chem., 1987, 52(15): 3326-3334.
Schaeffer and Schwartzberg, Curr Op Imm, 2000, 282-288.
Sic et al., Journal of Allergy and Clinical Immunology, 2014, 134(2): 420-428.

* cited by examiner

|  | Incidence (%) | Relapse (%) |
|---|---|---|
| Vehicle | 100 | 100 |
| (1) 0.3 mg/kg | 100 | 92 |
| (1) 1 mg/kg | 93 | 42 |
| (1) 3 mg/kg | 93 | 38 |

| | Relapse (%) |
|---|---|
| Vehicle | 100 |
| (1) 1 mg/kg | 80 |
| (1) 3 mg/kg | 60 |
| (1) 10 mg/kg | 50 |

Figure 5

| treatment regimen | Dose (mg/kg) | Incidence (%) | Relapse (%) | Time to relapse (mean; days) | # of relapses (mean) | Cumulative EAE score (mean) |
|---|---|---|---|---|---|---|
| Prophylactic | Veh | 100 | 100 | 27 | 1.3 | 101 |
| | 0.3 | 100 | 92 | 30 | 0.9 | 84 |
| | 1 | 93 | 42 | 38 * | 0.5 ** | 60 * |
| | 3 | 93 | 38 | 39 * | 0.4 *** | 42 *** |
| Therapeutic | Veh | n/a | 100 | 27 | 1.25 | 97 |
| | 1 | n/a | 80 | 33 | 0.9 | 93 |
| | 3 | n/a | 60 | 34 | 0.6 * | 90 |
| | 10 | n/a | 50 | 40 ** | 0.5 ** | 70 ** |

|  | EAE INCIDENCE (%) | RELAPSE (%) |
|---|---|---|
| Vehicle | 100 | 100 |
| (A225) 0.3 mg/kg | 93 | 73 |
| (A225) 1 mg/kg | 87 | 0 |
| (A225) 3 mg/kg | 53 | 0 |

Figure 11

1. Dose mice in the PLP model of EAE with Btk inhibitors
2. On Day 42 after the start of PLP and treatment give mice oral dose of compound.
3. Collect blood 2 hr and 24 hr after dosing (NDD)
4. Lyse RBCs and perform WBC treatment with biotinylated probe (ATB). Use 15 ul of blood for dried blood spot PK analysis (ATB). Analyze for CD69 upregulation (Yin Wu).
5. Lyse cells and perform streptavidin capture MSD Btk occupancy assay (ATB)
6. Measure plasma compound concentrations using dried blood spot analysis and low detection limit format (Hui Tian, Yi-Ying Chen)

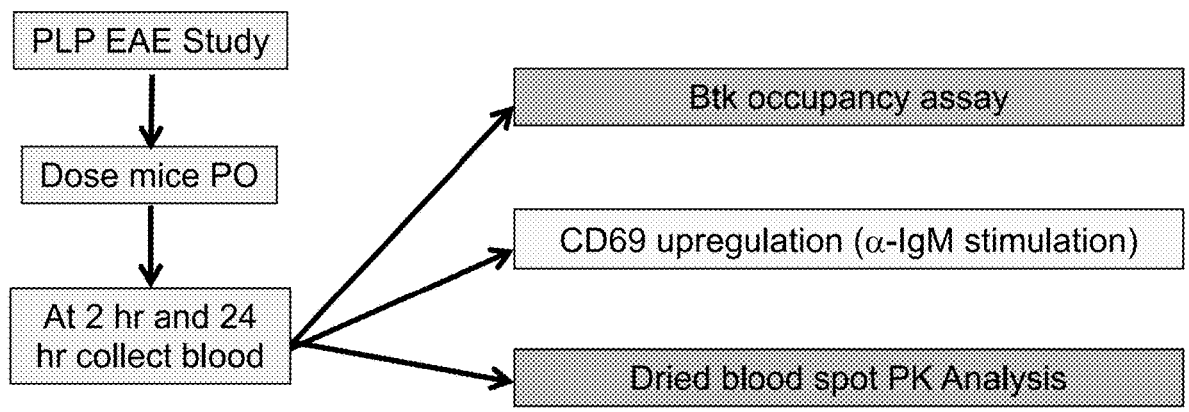

Figure 15 (c)

|  | RELAPSE BY END OF STUDY (%) |
|---|---|
| Vehicle | 100 |
| (A225) 1 mg/kg | 73 |
| (A225) 3 mg/kg | 80 |
| (A225) 10 mg/kg | 60 |

Figure 16

1. On day 10 after PLP treatment start to dose SJL mice in the PLP model of EAE with Btk inhibitors
2. On Day 43 after PLP treatment, administer mice an oral dose of compound (RN486 30 mg/kg, A225 dose response).
3. Collect blood 2 hr and 24 hr after dosing (NDD TC)
4. Lyse RBCs and perform WBC treatment with biotinylated probe (ATB). Use 15 ul of blood for dried blood spot PK analysis (ATB). Analyze for CD69 upregulation (ES).
5. Lyse cells and perform streptavidin capture MSD Btk occupancy assay (ATB)
6. Measure plasma compound concentrations using dried blood spot analysis and low detection limit format (HT, YC)

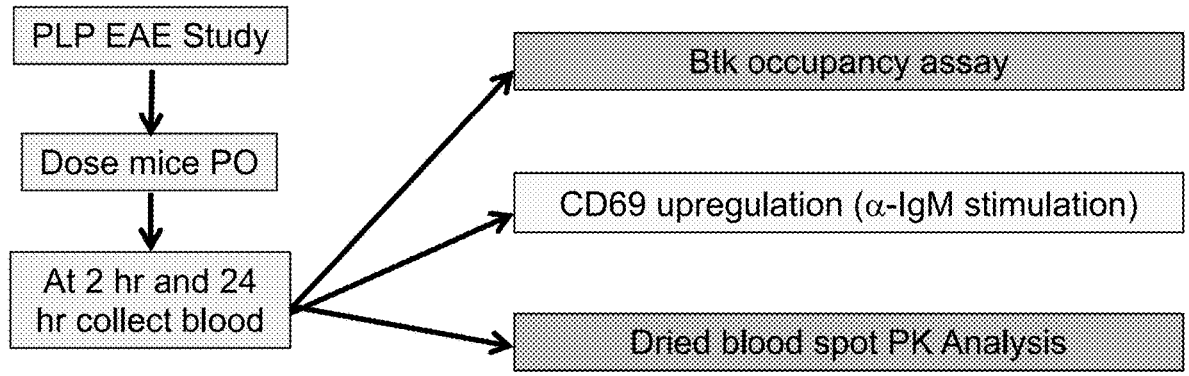

|  | 1st RELAPSE (%) | 2nd RELAPSE (%) |
|---|---|---|
| Vehicle | 100 | 70 |
| (A225) 1 mg/kg | 100 | 10 |
| (A225) 10 mg/kg | 80 | 10 |

Figure 21 (c)

|  | 1st RELAPSE (%) | 2nd RELAPSE (%) |
|---|---|---|
| Vehicle | 100 | 43 |
| (A225) 1 mg/kg | 67 | 20 |
| (A225) 10 mg/kg | 13 | 7 |

METHODS FOR TREATING MS USING PYRIMIDINE AND PYRIDINE COMPOUNDS WITH BTK INHIBITORY ACTIVITY

RELATED APPLICATIONS

This application claims the benefit of U.S. Provisional application No. 62/256,199, filed on Nov. 17, 2015, the contents of which are incorporated herein in its entirety, by reference.

FIELD OF THE INVENTION

The invention relates to a series of pyrimidine and pyridine compounds that are useful as therapeutics in the treatment of multiple sclerosis (MS) in mammals. More particularly, embodiments of the present invention describe irreversible kinase inhibitors including, but not limited to, inhibitors of Bruton's tyrosine kinase (hereinafter referred to as: "BTK"). Methods for the preparation of the aforementioned compounds are disclosed in addition to the incorporation of these compounds into pharmaceutical compositions that include the same.

BACKGROUND

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)). Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

BTK, a member of the Tec family of non-receptor tyrosine kinases, is a signaling enzyme expressed in all hematopoietic cells types except T lymphocytes and natural killer cells. BTK plays a well documented role in the B-cell signaling pathway linking cell surface B-cell receptor stimulation to downstream intracellular responses. BTK is also a regulator of B-cell development, activation, signaling, and survival (Kurosaki, Curr Op Imm, 2000, 276-281; Schaeffer and Schwartzberg, Curr Op Imm 2000, 282-288). In addition, BTK exerts a physiological effect through other hematopoetic cell signaling pathways, e.g., Toll like receptor (TLR) and cytokine receptor-mediated TNF-a production in macrophages, IgE receptor (FcepsilonR1) signaling in Mast cells, inhibition of Fas/APO-1 apoptotic signaling in B-lineage lymphoid cells, and collagen-stimulated platelet aggregation. BTK has an ATP-binding pocket with high similarity to Src-family kinases, such as lymphocyte-specific protein tyrosine kinase (Lck) and Lyn. Comparing BTK to other kinases one finds a conserved cysteine residue, Cys-481, in 11 of 491 kinases, specifically members of the Tec and EGFR (epidermal growth factor receptor) kinase families.

BTK plays important roles in the development, differentiation, activation and proliferation of B cells, as well as their antibody and cytokine generation. In addition, Btk plays a central role in other immunological processes such as cytokine production by neutrophils, mast cells and monocytes, degranulation of neutrophils and mast cells as well as differentiation/activation of osteoclasts. B-cell activation, break of tolerance and auto-antibody production, on one hand and the proinflammatory milieu originated from exacerbated activation of monocytes, neutrophils and mast cells, on the other hand, are crucial in the etiology of autoimmune diseases, including (but not limited to) rheumatoid arthritis and systemic lupus erythematosus.

Reversible kinase inhibitors have been developed into therapeutic compounds. These reversible inhibitors, however, have decided disadvantages. Many reversible inhibitors of kinases interact with the ATP-binding site. Given the structure of the ATP-binding sites are highly conserved among kinases, it has been difficult to develop a reversible inhibitor that selectively inhibits a desired (La, target) kinase. Moreover, given that many reversible kinase inhibitors readily dissociate from their target polypeptide(s), maintaining inhibition over extended periods of time can be difficult. When using reversible kinase inhibitors as therapeutics, therefore, often times near toxic dosages and/or frequent dosing is required to achieve the intended biological effect.

What is needed, therefore, are irreversible kinase inhibitors that covalently bind to their target polypeptide(s) without (substantially) binding to off-target polypeptides and, thereby, exerting undesirable off-target effects.

SUMMARY OF THE INVENTION

The present invention is directed towards compounds of the formulae presented herein for the treatment and/or prophylaxis of multiple sclerosis (MS), including relapsing MS (RMS), relapsing-remitting MS (RRMS), progressive MS (PMS), secondary-progressive MS (SPMS), primary-progressive MS (PPMS), and progressive-relapsing MS (PRMS).

DESCRIPTION OF THE FIGURES

FIG. 5: Summary table of clinical score data: compound (1).

FIG. 11: Compound (2) PK/PD Experimental design.

FIG. 16: Compound (2) Experimental design.

Figure 1:
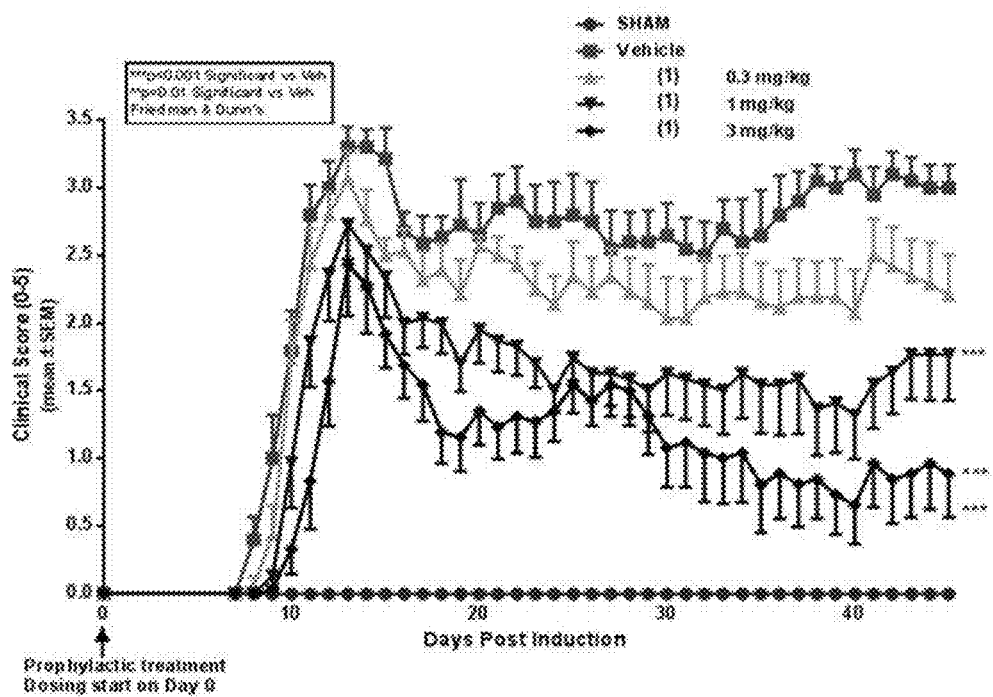
FIG. 1: (a) Prophylactic treatment with (1) delayed onset and reduced disease severity in SJL-EAE; (b) maximum clinical score at peak; (c) disease onset; (d) cumulative clinical score.
Figure 1:
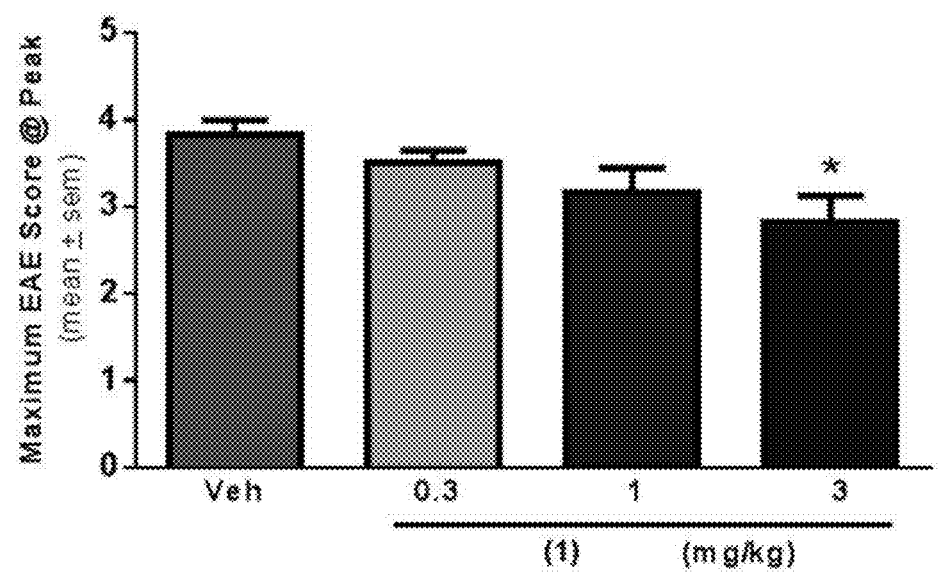
Figure 1:
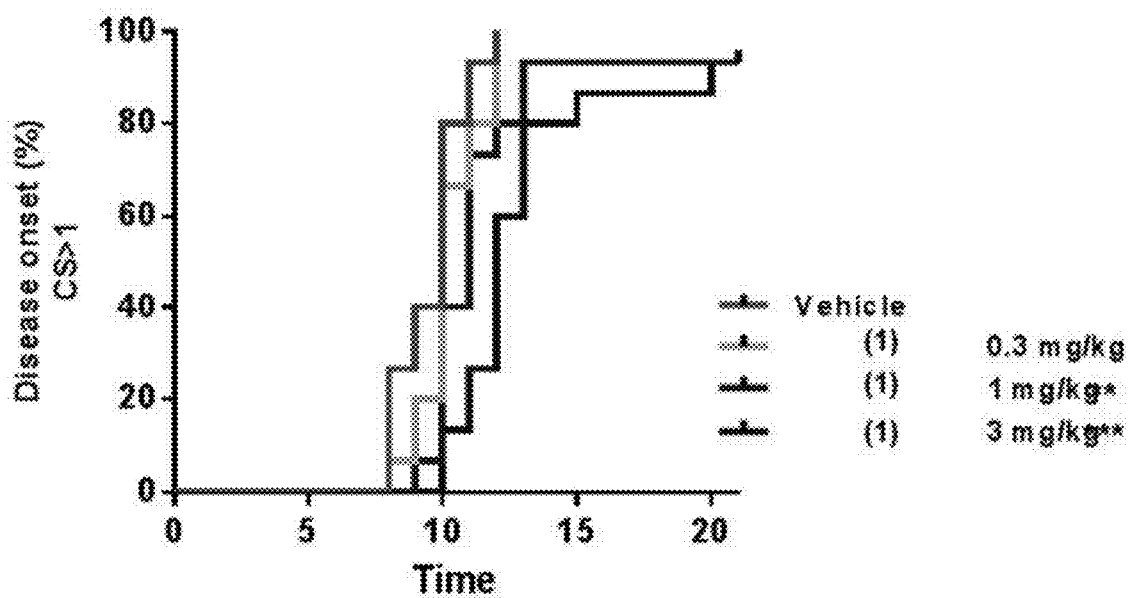
Figure 1:
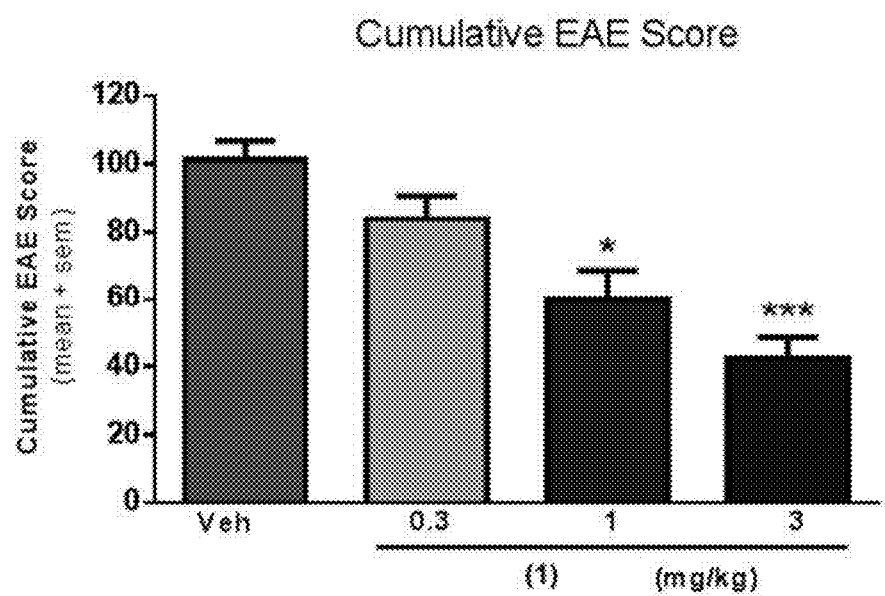

Throughout the specification and the figures, the terms compound (1) and compound (A250) are used interchangeably. Throughout the specification and the figures, the terms compound (2) and compound (A225) are used interchangeably.

DESCRIPTION OF THE INVENTION

The present invention provides a series of novel pyrimidine and pyridine kinase inhibitors. In some embodiments said kinase inhibitors are irreversible inhibitors of tyrosine kinases. In preferred embodiments, said irreversible kinase inhibitors inhibit BTK. While it is not intended that the compounds described by the present invention be limited to any specific mechanism of action, in some embodiments said irreversible kinase inhibitors exert a physiological effect by forming a covalent bond with Cys 481 in BTK. Significantly, this Cys 481 in BTK finds homologs in other kinases.

Embodiments of the present invention also described methods for synthesizing said irreversible inhibitors, methods for using said irreversible inhibitors in the treatment of diseases (including neurodegenerative diseases). Further described are pharmaceutical formulations that include an irreversible kinase inhibitor including pharmaceutically acceptable salts, solvates or prodrugs thereof, that are kinase inhibitors and useful in the treatment of the above mentioned diseases.

In one aspect, the invention provides a method for the treatment and/or prophylaxis of multiple sclerosis (MS), including relapsing MS (RMS), relapsing-remitting MS (RRMS), progressive MS (PMS), secondary-progressive MS (SPMS), primary-progressive MS (PPMS), and progressive-relapsing MS (PRMS), comprising administering to a subject a compound of Formula (I):

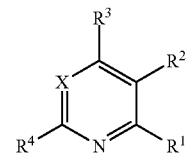

in which:
X denotes CH or N,
$R^1$ denotes $NH_2$, $CONH_2$ or H,
$R^2$ denotes Hal, $Ar^1$ or $Het^1$,
$R^3$ denotes $NR^5[C(R^5)_2]_nHet^2$, $NR^5[C(R^5)_2]_nCyc$, $Het^2$, $O[C(R^5)_2]_nAr^2$, $NR^5[C(R^5)_2]_nAr^2$, $O[C(R^5)_2]_nHet^2$, $NR^5(CH_2)_pNR^5R^6$, $O(CH_2)_pNR^5R^6$ or $NR^5(CH_2)_pCR^7R^8NR^5R^6$,
$R^4$ denotes H, $CH_3$ or $NH_2$,
$R^5$ denotes H or alkyl having 1, 2, 3 or 4 C atoms,
$R^6$ $N(R^5)_2CH_2CH=CHCONH$, $Het^3CH_2CH=CHCONH$, $CH_2=CHCONH(CH_2)_n$, $Het^4(CH_2)_nCOHet^3$-diyl-$CH_2CH=CHCONH$, $HC≡CCO$, $CH_3C≡CCO$, $CH_2≡CH-CO$, $CH_2=C(CH_3)CONH$, $CH_3CH=CHCONH(CH_2)_n$, $N≡CCR^7R^8CONH(CH_2)_n$, $Het^4NH(CH_2)_pCOHet^3$-diyl-$CH_2CH=CHCONH$, $Het^4(CH_2)_pCONH(CH_2CH_2O)_p(CH_2)_pCOHet^3$-diyl-$CH_2CH=CHCONH$, $CH_2=CHSO_2$, $ACH=CHCO$, $CH_3CH=CHCO$, $Het^4(CH_2)_pCONH(CH_2)_pHet^3$-diyl-$CH_2CH=CHCONH$, $Ar^3CH=CHSO_2$, $CH_2=CHSO_2NH$ or $N(R^5)CH_2CH=CHCO$,
$R^7$, $R^8$ denote together alkylene having 2, 3, 4, or 5 C atoms,
$Ar^1$ denotes phenyl or naphthyl, each of which is unsubstituted or mono-, di- or trisubstituted by $R^6$, Hal, $(CH_2)_nNH_2$, $CONHAr^3$, $(CH_2)_nNHCOA$, $O(CH_2)_nAr^3$, OCyc, A, $COHet^3$, OA and/or $OHet^3$ $(CH_2)$,
$Ar^2$ denotes phenyl, naphthyl or pyridyl each of which is unsubstituted or mono-, di- or trisubstituted by $R^6$, Hal, $OAr^3$, $(CH_2)_nNH_2$, $(CH_2)_nNHCOA$ and/or $Het^3$,
$Ar^3$ denotes phenyl, which is unsubstituted or mono-, di- or trisubstituted by OH, OA, Hal, CN and/or A,
$Het^1$ denotes a mono- or bicyclic saturated, unsaturated or aromatic heterocycle having 1 to 4 N, O and/or S atoms, which may be unsubstituted or mono-, di- or trisubstituted by $R^6$, $O(CH_2)_nAr^3$ and/or $(CH_2)_nAr^3$,
$Het^2$ denotes a mono- or bicyclic saturated heterocycle having 1 to 4 N, O and/or S atoms, which may be unsubstituted or mono-, di- or trisubstituted by $R^6$, $Het^3$, $CycSO_2$, OH, Hal, COOH, OA, COA, $COHet^3$, CycCO, $SO_2$ and/or =O, Het³ denotes a monocyclic unsaturated, saturated or aromatic heterocycle having 1 to 4 N, O and/or S atoms, which may be unsubstituted or mono-, di- or trisubstituted by Hal, A and/or =O, Het⁴ denotes a bi- or tricyclic unsaturated, saturated or aromatic heterocycle having 1 to 4 N, O and/or S atoms, which may be unsubstituted or mono-, di-, tri- or tetrasubstituted by A, NO₂, Hal and/or =O, Cyc denotes cyclic alkyl having 3, 4, 5 or 6 C atoms, which is unsubstituted, monosubstituted or disubstituted by R⁶ and/or OH and which may comprise a double bond, A denotes unbranched or branched alkyl having 1-10 C atoms, in which 1-7 H atoms may be replaced by F and/or Cl and/or in which one or two non-adjacent CH₂ and/or CH-groups may be replaced by O, NH and/or by N, Hal denotes F, Cl, Br or I, n denotes 0, 1, 2, 3 or 4, p denotes 1, 2, 3, 4, 5 or 6, and pharmaceutically usable salts, tautomers and stereoisomers thereof, including mixtures thereof in all ratios.

In general, all residues which occur more than once may be identical or different, i.e. are independent of one another. In other embodiments, the residues and parameters have the meanings indicated for the Formula (I), unless expressly indicated otherwise.

In certain embodiments, Het¹ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, azabicyclo[2.2.2]octyl, imidazolidinyl, azetidinyl, azepanyl, benzo-2,1,3-thiadiazolyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl, dihydropyridyl or dihydrobenzodioxinyl, each of which is unsubstituted or mono-, di- or trisubstituted by R⁶, O(CH₂)ₙAr³ and/or (CH₂)ₙAr³.

In certain embodiments, Het¹ denotes pyrazolyl, pyridyl, pyrimidinyl, dihydropyridyl or dihydrobenzodioxinyl, each of which is unsubstituted or mono-, di- or trisubstituted by R⁶, O(CH₂)ₙAr³ and/or (CH₂)ₙAr³.

In certain embodiments, Het² denotes piperidinyl, piperazinyl, pyrrolidinyl, morpholinyl, azabicyclo[3.2.1]octyl, azabicyclo[2.2.2]octyl, 2,7-diazaspiro[3.5]nonyl, 2,8-diazaspiro[4.5]decyl, 2,7-diazaspiro[4.4]nonyl, 3-azabicylo[3.1.0]hexyl, 2-[3.3]heptyl, 6-azaspiro[3.4]octyl, 7-azaspiro[3.5]nonyl, 5-azaspiro[3.5]nonyl, imidazolidinyl, azetidinyl, azepanyl, tetrahydrofuryl, dioxolanyl, tetrahydrothienyl, tetrahydroimidazolyl, tetrahydropyrazolyl, tetrahydropyridyl, each of which is unsubstituted or mono-, di- or trisubstituted by R⁶, Het³, CycSO₂, OH, OA, COA, COHet³, CycCO, SO₂ and/or =O.

In certain embodiments, Het³ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, imidazolidinyl, azetidinyl, azepanyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl or dihydropyridyl, each of which may be unsubstituted or mono-, di- or trisubstituted by Hal, A and/or =O.

In certain embodiments, Het³ denotes piperidinyl, pyrrolidinyl, morpholinyl, furyl, thienyl, pyrrolyl, imidazolyl, pyrazolyl, pyridyl, pyrimidinyl, dihydropyrrolyl, dihydropyrazolyl or dihydropyridyl, each of which may be unsubstituted or mono-, di- or trisubstituted by Hal, A and/or =O.

In certain embodiments, Het⁴ denotes hexahydrothieno[3,4-d]imidazolyl, benzo[c][1,2,5]oxadiazolyl or 5H-dipyrrolo[1,2-c:2',1'-f][1,3,2]diazaborinin-4-ium-uidyl, each of which may be unsubstituted or mono-, di-, tri- or tetrasubstituted by A, NO₂, Hal and/or =O.

In certain embodiments,

X denotes CH or N,

R¹ denotes NH₂, CON H₂ or H,

R² denotes Hal, Ar¹ or Het¹,

R³ denotes NR⁵[C(R⁵)₂]ₙHet², NR⁵[C(R⁵)₂]ₙCyc, Het², O[C(R⁵)₂]ₙAr², NR⁵[C(R⁵)₂]ₙAr², O[C(R⁵)₂]ₙHet², NR⁵(CH₂)ₚNR⁵R⁶, O(CH₂)ₚNR⁵R⁶ or NR⁵(CH₂)ₚCR⁷R⁸NR⁵R⁶, R⁴ denotes H, R⁵ denotes H or alkyl having 1, 2, 3 or 4 C atoms, R⁶ N(R⁵)₂CH₂CH=CHCONH, Het³CH₂CH=CHCONH, CH₂=CHCONH(CH₂)ₙ, Het⁴(CH₂)ₙCOHet³-diyl-CH₂CH=CHCONH, HC≡CCO, CH₃C≡CCO, CH₂=CH—CO, CH₂=C(CH₃)CONH, CH₃CH=CHCONH(CH₂)ₙ, N≡CCR⁷R⁸CONH(CH₂)ₙ, Het⁴NH(CH₂)ₚCOHet³-diyl-CH₂CH=CHCONH, Het⁴(CH₂)ₚCONH(CH₂CH₂O)ₚ(CH₂)ₚCOHet³-diyl-CH₂CH=CHCONH, CH₂=CHSO₂, ACH=CHCO, CH₃CH=CHCO, Het⁴(CH₂)ₚCONH(CH₂)ₚHet³-diyl-CH₂CH=CHCONH, Ar³CH=CHSO₂, CH₂=CHSO₂NH or N(R⁵)CH₂CH=CHCO, R⁷, R⁸ denote together alkylene having 2, 3, 4, or 5 C atoms, Ar¹ denotes phenyl or naphthyl, each of which is unsubstituted or mono-, di- or trisubstituted by R⁶, Hal, (CH₂)ₙNH₂, CONHAr³, (CH₂)ₙNHCOA, O(CH₂)ₙAr³, OCyc, A, COHet³, OA and/or OHet³ (CH₂), Ar² denotes phenyl or naphthyl, each of which is unsubstituted or mono-, di- or trisubstituted by R⁶, Hal, OAr³, (CH₂)ₙNH₂, (CH₂)ₙNHCOA and/or Het³, Ar³ denotes phenyl, which is unsubstituted or mono-, di- or trisubstituted by OH, OA, Hal, CN and/or A, Het¹ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, aza-bicyclo[2.2.2]octyl, imidazolidinyl, azetidinyl, azepanyl, benzo-2,1,3-thiadiazolyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl, dihydropyridyl or dihydrobenzodioxinyl, each of which is unsubstituted or mono-, di- or trisubstituted by R⁶, O(CH₂)ₙAr³ and/or (CH₂)ₙAr³, Het² denotes piperidinyl, piperazinyl, pyrrolidinyl, morpholinyl, azabicyclo[3.2.1]octyl, azabicyclo[2.2.2]octyl, 2,7-diazaspiro[3.5]nonyl, 2,8-diazaspiro[4.5]decyl, 2,7-diazaspiro[4.4]nonyl, 3-azabicylo[3.1.0]hexyl, 2-azaspiro[3.3]heptyl, 6-azaspiro[3.4]octyl, 7-azaspiro[3.5]nonyl, 5-azaspiro[3.5]nonyl, imidazolidinyl, azetidinyl, azepanyl, tetrahydrofuryl, dioxolanyl, tetrahydrothienyl, tetrahydroimidazolyl, tetrahydropyrazolyl, tetrahydropyridyl, each of which is unsubstituted or mono-, di- or trisubstituted by R⁶, Het³, CycSO₂, OH, OA, COA, COHet³, CycCO, SO₂ and/or =O, Het³ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, imidazolidinyl, azetidinyl, azepanyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl or dihydropyridyl, each of which may be unsubstituted or mono-, di- or trisubstituted by Hal, A and/or =O, Het⁴ denotes hexahydrothieno[3,4-d]imidazolyl, benzo[c][1,2,5]oxadiazolyl or 5H-dipyrrolo[1,2-c:2',1'-f][1,3,2]diazaborinin-4-ium-uidyl, each of which may be unsubstituted or mono-, di-, tri- or tetrasubstituted by A, NO₂, Hal and/or =O, Cyc denotes cyclic alkyl having 3, 4, 5 or 6 C atoms, which is unsubstituted or monosubstituted by R⁶ and which may comprise a double bond, A denotes unbranched or branched alkyl having 1-10 C atoms, in which 1-7 H atoms may be replaced by F and/or Cl and/or in which one or two non-adjacent CH₂ and/or CH-groups may be replaced by O, NH and/or by N, Hal denotes F, Cl, Br or I, n denotes 0, 1, 2, 3 or 4, p denotes 1, 2, 3, 4, 5 or 6.

In certain embodiments, the invention provides a method for the treatment and/or prophylaxis of multiple sclerosis (MS), including relapsing MS (RMS), relapsing-remitting MS (RRMS), progressive MS (PMS), secondary-progressive MS (SPMS), primary-progressive MS (PPMS), and progressive-relapsing MS (PRMS), comprising administering to a subject a compound of Formula (II):

Formula (II)

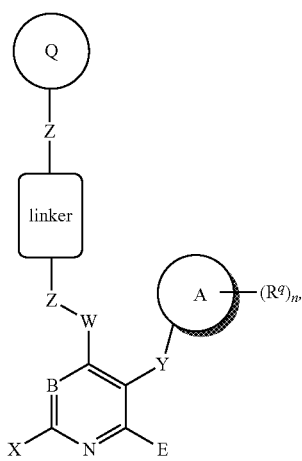

and pharmaceutically acceptable salts, solvates, solvates of salts, or prodrugs thereof, wherein:

X is H or CH₃ or NH₂,

Y is H, Hal or is absent,

B is N or CH,

E is NH₂ or H,

W is NR, 0 or a cyclic amine,

Z is, independently, CH₂, CH₃, CH₂—CH₂, CH—CH₂, H, NH or is absent,

"linker" is (CH₂)ₙ, wherein: ₙ is 1, 2 or 3 or an optionally substituted group selected from a phenyl ring, an aryl ring, heteroaryl ring, branched or unbranched alkyl group, a 5-6 membered monocyclic heteroaryl ring having 1-4 heteroatoms independently selected from nitrogen, or oxygen, a 4-7 membered saturated or partially unsaturated heterocycle having 1-3 heteroatoms independently selected from nitrogen, or oxygen, or a 7-10 membered bicyclic saturated or partially unsaturated heterocyclic ring having 1-5 heteroatoms independently selected from nitrogen, or oxygen, or a 7-10 membered bicyclic saturated or partially unsaturated heterocyclic ring having 1-5 heteroatoms attached to a hetero saturated ring. Linkers may also be cycloalkanes optionally substituted by heteroatoms (independently selected from nitrogen, or oxygen), cycloalkanes optionally substituted with —NH or OH, fused or bridged rings or optionally substituted spirocyclic rings that optionally contain heteroatoms, A is a mono- or bicyclic aromatic homo- or heterocycle having 0, 1, 2, 3 or 4 N, and/or O atoms and 5, 6, 7, 8, 9, or 10 skeleton C atoms, which may be unsubstituted or, independently of one another, mono-, di- or trisubstituted by Hal, OH or OR, Hal is F, Cl, Br or I, R is independently hydrogen, oxygen or an optionally substituted group selected from $C_{1-6}$ linear or cyclic aliphatic, benzyl, phenyl, a phenyl group optionally substituted with 1, 2 or 3 O atoms, a 4-7 membered heterocyclic ring having 1-2 heteroatoms independently selected from nitrogen, oxygen, or a 5-6 membered monocyclic heteroaryl ring having 1-4 heteroatoms independently selected from nitrogen, or oxygen or a mono- or bicyclic aromatic homo- or heterocycle having 0, 1, 2, 3 or 4 N, O atoms and 5, 6, 7, or 8 C skeleton atoms, which may be unsubstituted or, independently of one another, mono-, di- or trisubstituted by Hal, A, OH, NH₂, nitrile, and/or CH(Hal)₃ or is an unbranched or branched linear alkyl having 1, 2, 3, 4, 5, 6, 7 or 8 C atoms, in which one or two CH₂ groups may be replaced by an O atom and/or by an —NH—, —CO—, —NHCOO—, —NHCONH—, —CONH—, —NHCO— or —CH=CH— group, and in which 1-3 H atoms may be replaced by Hal, $R^q$ is selected from —R, -A, halogen, —OR, —O(CH₂)ᵣOR, —R(NH), —NO₂, —C(O)R, —CO₂R, —C(O)N(R)₂, —NRC(O)R, —NRC(O)NR₂, —NRSO₂R, or —N(R)₂, r is 1-4, n is 0-4, and Q is an electrophilic group such as those listed in Table 1 wherein said electrophilic groups may further comprise a warhead.

As used herein the term "warhead" refers to a part, functional group or substituent of the compounds as claimed in the present invention, wherein, said part, functional group or substituent covalently binds to an amino acid (such as cysteine, lysine, or any other amino acid, either native or modified, that can form said covalent bond) that is present, for example, in the binding region within a given ligand wherein said warhead binds with said ligand, wherein the covalent binding between said warhead and the binding region of said target protein occurs under conditions wherein a physiological function of said protein is irreversibly inhibited.

While it is not intended that the present invention be limited to a specific group for subtituent Q, as set out in Formula (II) above, in certain embodiments substituent Q is selected from the groups set out in Table 1. All compounds, in Table 1, appearing within a box are not "warheads" as defined above.

TABLE 1
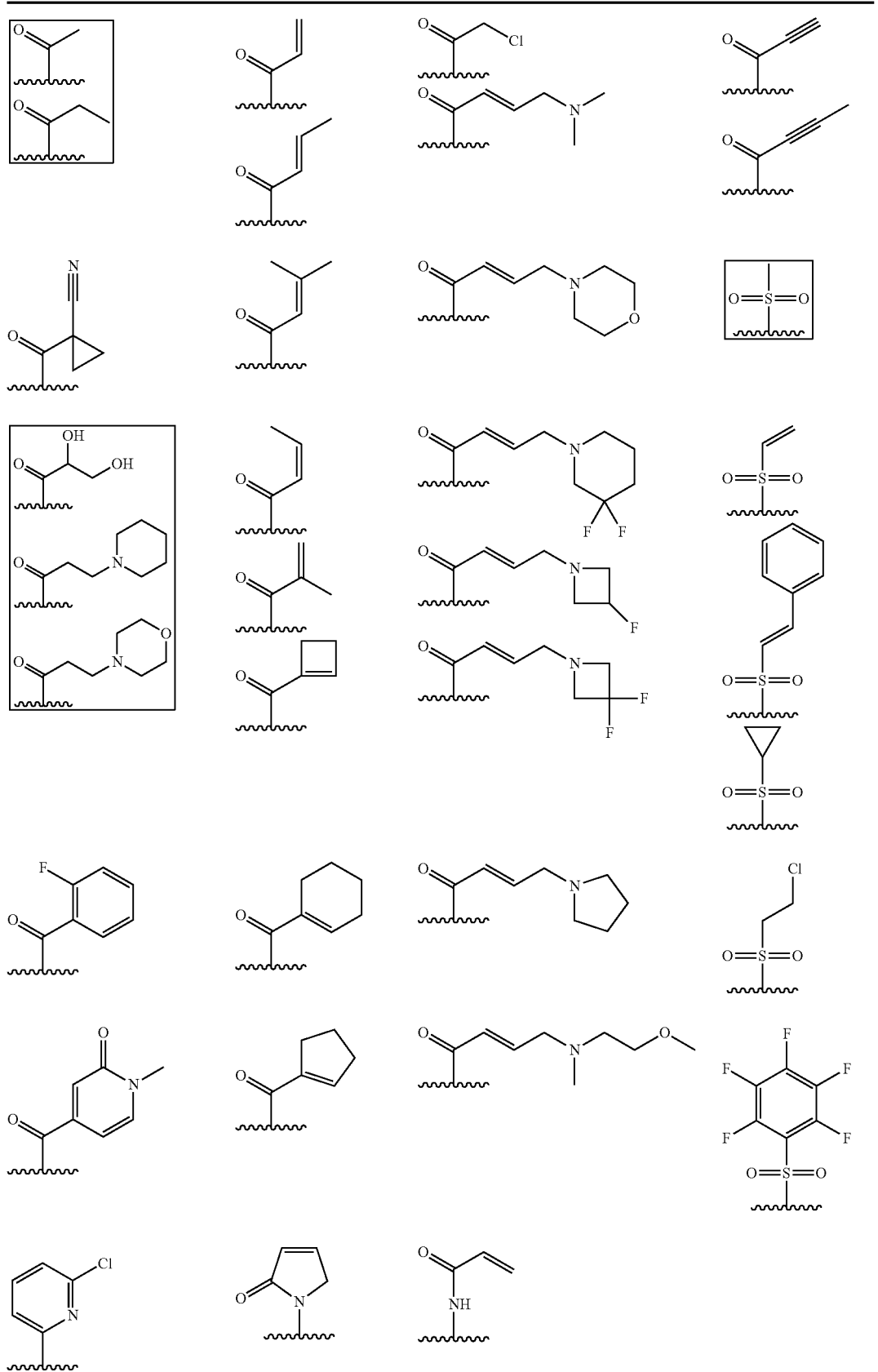

TABLE 1-continued

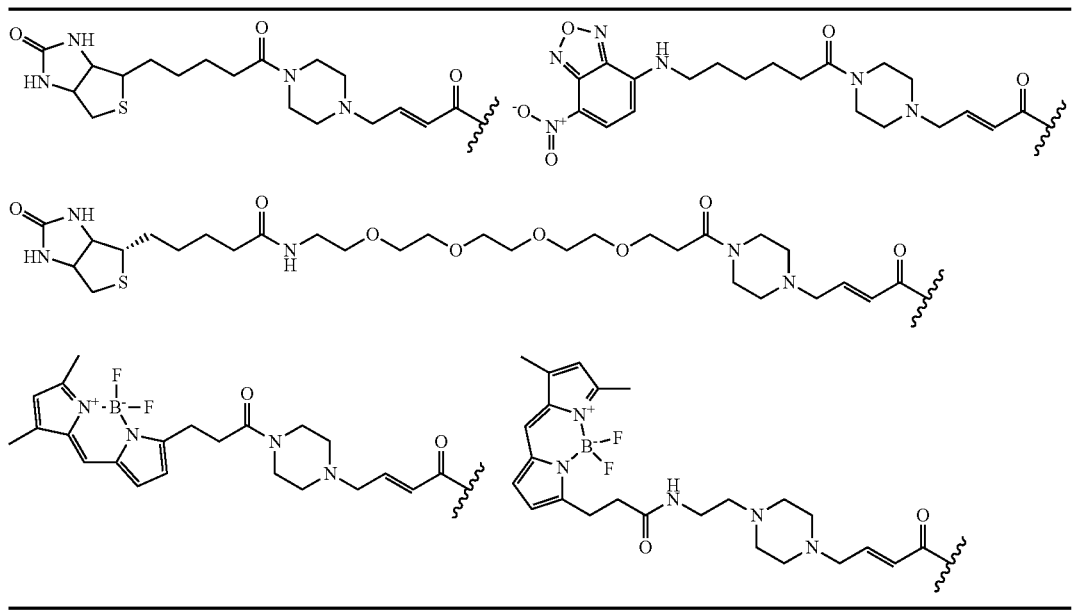

wherein, "∿∿∿" denotes the bonding point of Q to Z in Formula (II).

In certain embodiments, the invention provides a method for the treatment and/or prophylaxis of multiple sclerosis (MS), including relapsing MS (RMS), relapsing-remitting MS (RRMS), progressive MS (PMS), secondary-progressive MS (SPMS), primary-progressive MS (PPMS), and progressive-relapsing MS (PRMS), comprising administering to a subject a compound of Formula (III):

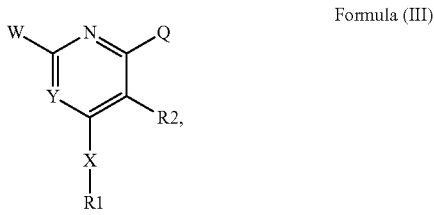

Formula (III)

and pharmaceutically acceptable salts, solvates, solvates of salts, or prodrugs thereof, wherein:
X is O or NH,
Y is N or CH,
W is H, $NH_2$ or $CONH_2$,
Q is H or $NH_2$,
$R^1$ is $L^1$-$R^4$-$L^2$-$R^5$,
$R^2$ is $M^1$-$S^4$-$M^2$-$S^5$
$L^1$ is a single bond, methylene, or cyclic A which may be mono- or disubstituted with N or $NH_2$,
$R^4$ is Ar, A or cyclic A which may be mono- or disubstituted with N, —O— or Hal,
$R^5$ is Ar, A or cyclic A which may be mono- or disubstituted with N, —O— or
Hal or is absent. In preferred embodiments, $R^5$ is selected from the group consisting of 2-fluoropyridine, 1-methylpyridin-2(1H)-one and 2-chloropyridine,
$L^2$ is H, —O—, substituted or unsubstituted $C_1$-$C_4$alkyl, substituted or unsubstituted $C_1$-$C_4$ heteroalkyl, $C_1$-$C_6$alkoxyalkyl, $C_1$-$C_8$alkylaminoalkyl, substituted or unsubstituted aryl, substituted or unsubstituted heteroaryl, $C_1$-$C_4$alkyl(aryl), $C_1$-$C_4$alkyl(heteroaryl), $C_1$-$C_4$alky($C_3$-$C_8$cycloalkyl), or $C_1$-$C_4$alkyl($C_2$-$C_8$heterocycloalkyl). In some embodiments, $L^2$ is —$CH_2$—O—($C_1$-$C_3$alkyl), —$CH_2$—N($C_1$-$C_3$alkyl)$_2$, $C_1$-$C_4$alkyl(phenyl), or $C_1$-$C_4$alkyl (5- or 6-membered heteroaryl). In some embodiments $L^2$ is -A-. In some embodiments $L^2$ is absent. In preferred embodiments of the present invention $L^2$ is selected from the group consisting of but-3-en-2-one, propan-2-one, (E)-5-(dimethylamino)pent-3-en-2-one, (E)-pent-3-en-2-one, pent-3-yn-2-one, 1-chloropropan-2-one, (methylsulfonyl)ethane, (E)-5-((2-methoxyethyl)(methyl)amino)pent-3-en-2-one or (Z)-pent-3-en-2-one,
$M^1$ is a single bond,
$S^4$ is Ar, A or cyclic A which may be mono- or disubstituted with N, —O— or Hal. In preferred embodiments of the present invention $S^4$ is a heteroaromatic 5 to 6 member ring,
$M^2$ O, NH, $CH_2$ or is absent,
$S^5$ is H, Ar, A or cyclic A which may be mono- or disubstituted with N, —O—, Hal. In certain embodiments of the present invention $S^5$ is selected from the group consisting of but-3-en-2-one, benzene, (E)-5-(dimethylamino)pent-3-en-2-one, ethylbenzene, 1-ethyl-2-methoxybenzene, aniline and (E)-5-morpholinopent-3-en-2-one. In some embodiments of the present invention $S_5$ is absent,
Ar is a mono- or bicyclic aromatic homo- or heterocycle having 0, 1, 2, 3 or 4 N, and/or O atoms and 5, 6, 7, 8, 9, or 10 skeleton atoms, which may be unsubstituted or, independently of one another, mono-, di- or trisubstituted by Hal, A, OH, OA, $NH_2$, NHA, $NA_2$, $NO_2$, CN, OCN, COOH, COOA, $CONH_2$, CONHA, $CONA_2$, NHCOA, NHCONHA, NHCONH, CHO and/or COA, and in which a ring N-atom may be substituted by an O-atom to form an N-oxide group and in which in the case of a bicyclic aromatic cycle on of the two rings may be partly saturated,
A is unbranched or branched linear or cyclic alkyl having 1, 2, 3, 4, 5, 6, 7 or 8 C atoms, in which one or two $CH_2$ groups may be replaced by an O atom and/or by an —NH—, —CO—, —NHCOO—, —NHCONH—. —N(LA)-, —CONH—, —NHCO— or —CH═CH— group, LA is unbranched or branched, linear alkyl having 1, 2, 3 or 4 C atoms, wherein 1, 2 or 3 H atoms may be replaced by Hal, Hal is F, Cl, Br or I.

In certain embodiments, the invention provides a method for the treatment and/or prophylaxis of multiple sclerosis (MS), including relapsing MS (RMS), relapsing-remitting MS (RRMS), progressive MS (PMS), secondary-progressive MS (SPMS), primary-progressive MS (PPMS), and progressive-relapsing MS (PRMS), comprising administering to a subject a compound of Formula (IV):

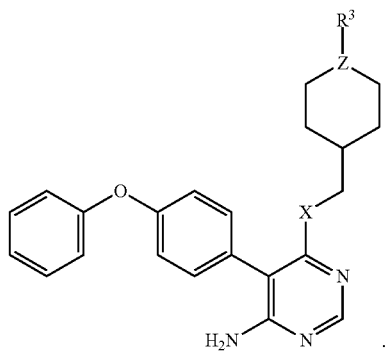

Formula (IV)

and pharmaceutically acceptable salts, solvates, solvates of salts, or prodrugs thereof, wherein:

Z is N or CH,

X is O or NH, and $R^3$ is selected from the group consisting of the following structures:

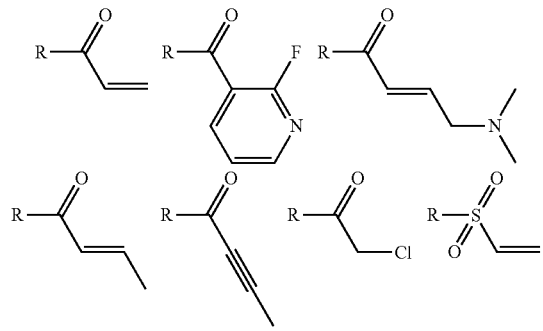

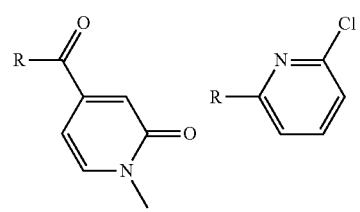

-continued

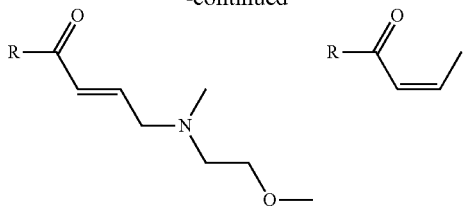

wherein, "R" denotes the bonding point to Z in Formula IV.

In certain embodiments, the invention provides a method for the treatment and/or prophylaxis of multiple sclerosis (MS), including relapsing MS (RMS), relapsing-remitting MS (RRMS), progressive MS (PMS), secondary-progressive MS (SPMS), primary-progressive MS (PPMS), and progressive-relapsing MS (PRMS), comprising administering to a subject a compound of Formula (V):

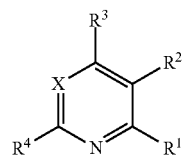

V and pharmaceutically acceptable salts, solvates, solvates of salts, or prodrugs thereof, in which:

X denotes CH or N, $R^1$ denotes $NR^5[C(R^5)_2]_n Het^2$, $R^2$ denotes Hal, $Ar^1$ or $Het^1$, $R^3$ denotes $NH_2$, $R^4$ denotes H, $CH_3$ or $NH_2$, $R^5$ denotes H or alkyl having 1, 2, 3 or 4 C atoms, $R^6$   $N(R^5)_2CH_2CH$═CHCONH,   $Het^3CH_2CH$═CH-CONH, $CH_2$═CHCONH$(CH_2)_n$, $Het^4(CH_2)_n$COHet$^3$-diyl-CH$_2$CH═CHCONH,   HC≡CCO,   CH$_3$C≡CCO, CH$_2$═CH—CO,   CH$_2$═C(CH$_3$)CONH,   CH$_3$CH═CHCONH(CH$_2)_n$, N≡CCR$^7$R$^8$CONH(CH$_2)_n$,   Het$^4$NH (CH$_2)_p$COHet$^3$-diyl-CH$_2$CH═CHCONH, Het$^4$(CH$_2)_p$CONH(CH$_2$CH$_2$O$)_p$(CH$_2)_p$COHet$^3$-diyl-CH$_2$CH═CHCONH,   CH$_2$═CHSO$_2$,   ACH═CHCO, CH$_3$CH═CHCO, Het$^4$(CH$_2)_p$CONH(CH$_2)_p$Het$^3$-diyl-CH$_2$CH═CHCONH, Ar$^3$CH═CHSO$_2$, CH$_2$═CHSO$_2$NH or $N(R^5)CH_2CH$═CHCO, $R^7$, $R^8$ denote together alkylene having 2, 3, 4, or 5 C atoms, Ar$_1$ denotes phenyl or naphthyl, each of which is unsubstituted or mono-, di- or trisubstituted by $R^6$, Hal, $(CH_2)_nNH_2$, CONHAr$^3$, $(CH_2)_n$NHCOA, O$(CH_2)_n$Ar$^3$, OCyc, A, COHet$^3$, OA and/or OHet$^3$ $(CH_2)$, Ar$^2$ denotes phenyl, naphthyl or pyridyl each of which is unsubstituted or mono-, di- or trisubstituted by $R^6$, Hal, OAr$^3$, $(CH_2)_nNH_2$, $(CH_2)_n$NHCOA and/or Het$^3$, Ar$^3$ denotes phenyl, which is unsubstituted or mono-, di- or trisubstituted by OH, OA, Hal, CN and/or A, Het$^1$ denotes a mono- or bicyclic saturated, unsaturated or aromatic heterocycle having 1 to 4 N, O and/or S atoms, which may be unsubstituted or mono-, di- or trisubstituted by $R^6$, O$(CH_2)_n$Ar$^3$ and/or $(CH_2)_n$Ar$^3$, Het² denotes a mono- or bicyclic saturated heterocycle having 1 to 4 N, O and/or S atoms, which may be unsubstituted or mono-, di- or trisubstituted by R⁶, Het³, CycSO₂, OH, Hal, COOH, OA, COA, COHet³, CycCO, SO₂ and/or =O, Het³ denotes a monocyclic unsaturated, saturated or aromatic heterocycle having 1 to 4 N, O and/or S atoms, which may be unsubstituted or mono-, di- or trisubstituted by Hal, A and/or =O, Het⁴ denotes a bi- or tricyclic unsaturated, saturated or aromatic heterocycle having 1 to 4 N, O and/or S atoms, which may be unsubstituted or mono-, di-, tri- or tetrasubstituted by A, NO₂, Hal and/or =O, Cyc denotes cyclic alkyl having 3, 4, 5 or 6 C atoms, which is unsubstituted, monosubstituted or disubstituted by R⁶ and/or OH and which may comprise a double bond, A denotes unbranched or branched alkyl having 1-10 C atoms, in which 1-7 H atoms may be replaced by F and/or Cl and/or in which one or two non-adjacent CH₂ and/or CH-groups may be replaced by O, NH and/or by N, Hal denotes F, Cl, Br or I, n denotes 0, 1, 2, 3 or 4, p denotes 1, 2, 3, 4, 5 or 6, and pharmaceutically usable salts, tautomers and stereoisomers thereof, including mixtures thereof in all ratios.

In certain embodiments, the invention provides a method for the treatment and/or prophylaxis of multiple sclerosis (MS), including relapsing MS (RMS), relapsing-remitting MS (RRMS), progressive MS (PMS), secondary-progressive MS (SPMS), primary-progressive MS (PPMS), and progressive-relapsing MS (PRMS), comprising administering to a subject a compound selected from Table 2:

TABLE 2

| No. | Chemical Name |
|---|---|
| "A1" | (R)-1-(3-((6-amino-5-(4-phenoxyphenyl)pyrimidin-4-yl)amino)pyrrolidin-1-yl)prop-2-en-1-one |
| "A2" | (R)-1-(3-((6-amino-5-(4-phenoxyphenyl)pyrimidin-4-yl)oxy)piperidin-1-yl)prop-2-en-1-one |
| "A3" | N-(3-((6-amino-5-(4-phenoxyphenyl)pyrimidin-4-yl)amino)phenyl)acrylamide |
| "A4" | (R)-1-(3-(((6-amino-5-(4-phenoxyphenyl)pyrimidin-4-yl)amino)methyl)pyrrolidin-1-yl)prop-2-en-1-one |
| "A5" | N-((1-(6-amino-5-(4-phenoxyphenyl)pyrimidin-4-yl)pyrrolidin-3-yl)methyl)acrylamide |
| "A6" | 1-(4-(((5-(4-phenoxyphenyl)pyrimidin-4-yl)oxy)methyl)piperidin-1-yl)prop-2-en-1-one |
| "A7" | N-((1-(6-amino-5-(4-phenoxyphenyl)pyrimidin-4-yl)piperidin-4-yl)methyl)acrylamide |
| "A8" | 4-(4-(((6-amino-5-(4-phenoxyphenyl)pyrimidin-4-yl)amino)methyl)piperidine-1-carbonyl)-1-methylpyridin-2(1H)-one |
| "A9" | 1-(4-(((6-amino-5-(4-phenoxyphenyl)pyrimidin-4-yl)oxy)methyl)piperidin-1-yl)but-2-yn-1-one |
| "A10" | 5-(4-phenoxyphenyl)-N4-((1-(vinylsulfonyl)piperidin-4-yl)methyl)pyrimidine-4,6-diamine |
| "A11" | (E)-1-(4-(((6-amino-5-(4-phenoxyphenyl)pyrimidin-4-yl)amino)methyl)piperidin-1-yl)-4-((2-methoxyethyl)(methyl)amino)but-2-en-1-one |
| "A12" | (4-(((6-amino-5-(4-phenoxyphenyl)pyrimidin-4-yl)amino)methyl)piperidin-1-yl)(2-fluoropyridin-3-yl)methanone |
| "A13" | (E)-1-(4-(((6-amino-5-(4-phenoxyphenyl)pyrimidin-4-yl)amino)methyl)piperidin-1-yl)but-2-en-1-one |
| "A14" | N4-((1-(cyclopropylsulfonyl)piperidin-4-yl)methyl)-5-(4-phenoxyphenyl)pyrimidine-4,6-diamine |
| "A15" | (Z)-1-(4-(((6-amino-5-(4-phenoxyphenyl)pyrimidin-4-yl)amino)methyl)piperidin-1-yl)but-2-en-1-one |
| "A16" | 1-(4-(2-((6-amino-5-(4-phenoxyphenyl)pyrimidin-4-yl)amino)ethyl)piperidin-1-yl)prop-2-en-1-one |
| "A17" | 1-(3-(((6-amino-5-(4-phenoxyphenyl)pyrimidin-4-yl)oxy)methyl)piperidin-1-yl)prop-2-en-1-one |
| "A18" | N-(2-((6-amino-5-(4-phenoxyphenyl)pyrimidin-4-yl)amino)ethyl)acrylamide |
| "A19" | (R)-1-(3-((6-amino-5-(4-phenoxyphenyl)pyrimidin-4-yl)oxy)pyrrolidin-1-yl)prop-2-en-1-one |
| "A20" | N-(1-(((6-amino-5-(4-phenoxyphenyl)pyrimidin-4-yl)amino)methyl)cyclopentyl)acrylamide |
| "A21" | 1-(3-(((6-amino-5-(4-phenoxyphenyl)pyrimidin-4-yl)oxy)methyl)pyrrolidin-1-yl)prop-2-en-1-one |
| "A22" | 1-(4-(((5-fluoro-3-(4-phenoxyphenyl)pyridin-2-yl)amino)methyl)piperidin-1-yl)prop-2-en-1-one |
| "A23" | 1-(4-(((6-amino-5-(4-phenoxyphenyl)pyrimidin-4-yl)amino)methyl)piperidin-1-yl)ethanone |
| "A24" | (E)-7-(3-(4-(4-((3-((6-amino-5-(4-phenoxyphenyl)pyrimidin-4-yl)oxy)phenyl)amino)-4-oxobut-2-en-1-yl)piperazin-1-yl)-3-oxopropyl)-5,5-difluoro-1,3-dimethyl-5H-dipyrrolo[1,2-c: 2',1'-f][1,3,2]diazaborinin-4-ium-5-uide |
| "A25" | 1-(4-(((2-amino-5-(4-phenoxyphenyl)pyrimidin-4-yl)amino)methyl)piperidin-1-yl)prop-2-en-1-one |
| "A26" | (S)-1-(3-(((6-amino-5-(4-phenoxyphenyl)pyrimidin-4-yl)oxy)methyl)pyrrolidin-1-yl)prop-2-en-1-one |

TABLE 2-continued

| No. | Chemical Name |
|---|---|
| "A27" | N-(2-((6-amino-5-(4-phenoxyphenyl)pyrimidin-4-yl)oxy)ethyl)acrylamide |
| "A28" | (S)-1-(3-(((6-amino-5-(4-phenoxyphenyl)pyrimidin-4-yl)amino)methyl)pyrrolidin-1-yl)prop-2-en-1-one |
| "A29" | 1-(4-(((6-amino-5-(4-phenoxyphenyl)pyrimidin-4-yl)amino)methyl)piperidin-1-yl)-2-methylprop-2-en-1-one |
| "A30" | (4-(((6-amino-5-(4-phenoxyphenyl)pyrimidin-4-yl)amino)methyl)piperidin-1-yl)(cyclohex-1-en-1-yl)methanone |
| "A31" | 1-(4-(((6-amino-5-(4-phenoxyphenyl)pyrimidin-4-yl)amino)methyl)piperidin-1-yl)-3-methylbut-2-en-1-one |
| "A32" | (4-(((6-amino-5-(4-phenoxyphenyl)pyrimidin-4-yl)amino)methyl)piperidin-1-yl)(cyclopent-1-en-1-yl)methanone |
| "A33" | 1-(4-(((6-amino-5-(1-benzyl-1H-pyrazol-4-yl)pyrimidin-4-yl)amino)methyl)piperidin-1-yl)prop-2-en-1-one |
| "A34" | 1-(4-(((6-amino-5-(4-(3-fluorophenoxy)phenyl)pyrimidin-4-yl)amino)methyl)piperidin-1-yl)prop-2-en-1-one |
| "A35" | (E)-7-(3-((2-(4-(4-((3-((6-amino-5-(4-phenoxyphenyl)pyrimidin-4-yl)oxy)phenyl)amino)-4-oxobut-2-en-1-yl)piperazin-1-yl)ethyl)amino)-3-oxopropyl)-5,5-difluoro-1,3-dimethyl-5H-dipyrrolo[1,2-c: 2',1'-f][1,3,2]diazaborinin-4-ium-5-uide |
| "A36" | 1-(4-(((6-amino-2-methyl-5-(4-phenoxyphenyl)pyrimidin-4-yl)amino)methyl)piperidin-1-yl)prop-2-en-1-one |
| "A37" | 1-(4-(((6-amino-5-(4-phenoxyphenyl)pyrimidin-4-yl)amino)methyl)-4-hydroxypiperidin-1-yl)prop-2-en-1-one |
| "A38" | (R)-1-(3-(((6-amino-5-(4-phenoxyphenyl)pyrimidin-4-yl)oxy)methyl)pyrrolidin-1-yl)prop-2-en-1-one |
| "A39" | 1-(4-(((6-amino-5-(4-(phenylamino)phenyl)pyrimidin-4-yl)amino)methyl)piperidin-1-yl)prop-2-en-1-one |
| "A40" | 1-(3-((6-amino-5-(4-phenoxyphenyl)pyrimidin-4-yl)oxy)phenyl)-1H-pyrrol-2(5H)-one |
| "A41" | 1-(4-(((6-amino-5-(4-benzylphenyl)pyrimidin-4-yl)amino)methyl)piperidin-1-yl)prop-2-en-1-one |
| "A42" | (4-(((6-amino-5-(4-phenoxyphenyl)pyrimidin-4-yl)amino)methyl)piperidin-1-yl)(cyclobut-1-en-1-yl)methanone |
| "A43" | (Z)-1-(4-(((6-amino-5-(4-phenoxyphenyl)pyrimidin-4-yl)oxy)methyl)piperidin-1-yl)but-2-en-1-one |
| "A44" | 1-(4-(((6-amino-2-methyl-5-(4-phenoxyphenyl)pyrimidin-4-yl)(methyl)amino)methyl)piperidin-1-yl)prop-2-en-1-one |
| "A45" | 1-(4-(((6-amino-5-(4-phenoxyphenyl)pyrimidin-4-yl)amino)methyl)piperidin-1-yl)-2-chloroethanone |
| "A46" | 1-(4-(((6-amino-5-(4-phenoxyphenyl)pyrimidin-4-yl)amino)methyl)piperidin-1-yl)prop-2-yn-1-one |
| "A47" | 1-(4-(((6-amino-5-(4-phenoxyphenyl)pyrimidin-4-yl)(methyl)amino)methyl)piperidin-1-yl)prop-2-en-1-one |
| "A48" | 1-(3-(((6-amino-5-(4-phenoxyphenyl)pyrimidin-4-yl)amino)methyl)-8-azabicyclo[3.2.1]octan-8-yl)prop-2-en-1-one |
| "A49" | N-((1S,3S)-3-((6-amino-5-(4-phenoxyphenyl)pyrimidin-4-yl)amino)cyclopentyl)acrylamide |
| "A50" | N-(4-((6-amino-5-(4-phenoxyphenyl)pyrimidin-4-yl)amino)butyl)acrylamide |
| "A51" | N-(cis-3-((6-amino-5-(4-phenoxyphenyl)pyrimidin-4-yl)amino)cyclohexyl)acrylamide |
| "A52" | 1-(3-((6-amino-5-(4-phenoxyphenyl)pyrimidin-4-yl)amino)azepan-1-yl)prop-2-en-1-one |
| "A53" | N-(trans-3-((6-amino-5-(4-phenoxyphenyl)pyrimidin-4-yl)amino)cyclohexyl)acrylamide |
| "A54" | (E)-5-(4-phenoxyphenyl)-N4-((1-(styrylsulfonyl)piperidin-4-yl)methyl)pyrimidine-4,6-diamine |
| "A55" | N4-((1-(methylsulfonyl)piperidin-4-yl)methyl)-5-(4-phenoxyphenyl)pyrimidine-4,6-diamine |
| "A56" | 1-(4-(((6-amino-5-(4-phenoxyphenyl)pyrimidin-4-yl)amino)methyl)piperidin-1-yl)-2,3-dihydroxypropan-1-one |
| "A57" | 4-(((6-amino-5-(4-phenoxyphenyl)pyrimidin-4-yl)amino)methyl)piperidin-2-one |
| "A58" | N-(3-((6-amino-5-(4-phenoxyphenyl)pyrimidin-4-yl)oxy)phenyl)ethenesulfonamide |
| "A59" | N-(3-((6-amino-5-(4-phenoxyphenyl)pyrimidin-4-yl)amino)propyl)acrylamide |
| "A60" | N-(5-((6-amino-5-(4-phenoxyphenyl)pyrimidin-4-yl)oxy)pyridin-3-yl)acrylamide |
| "A61" | (R)-1-(3-(((6-amino-5-(4-phenoxyphenyl)pyrimidin-4-yl)amino)methyl)pyrrolidin-1-yl)prop-2-yn-1-one |
| "A62" | (R,E)-1-(3-(((6-amino-5-(4-phenoxyphenyl)pyrimidin-4-yl)amino)methyl)pyrrolidin-1-yl)-4-(dimethylamino)but-2-en-1-one |
| "A63" | (E)-N-(cis-3-((6-amino-5-(4-phenoxyphenyl)pyrimidin-4-yl)amino)cyclohexyl)-4-(dimethylamino)but-2-enamide |

TABLE 2-continued

| No. | Chemical Name |
|---|---|
| "A64" | N-(cis-3-((6-amino-5-(4-phenoxyphenyl)pyrimidin-4-yl)amino)cyclohexyl)propiolamide |
| "A65" | (S)-1-(2-(((6-amino-5-(4-phenoxyphenyl)pyrimidin-4-yl)oxy)methyl)morpholino)prop-2-en-1-one |
| "A66" | (R)-1-(2-(((6-amino-5-(4-phenoxyphenyl)pyrimidin-4-yl)oxy)methyl)morpholino)prop-2-en-1-one |
| "A67" | N-(3-((6-amino-5-(1-(3-fluorobenzyl)-1H-pyrazol-4-yl)pyrimidin-4-yl)oxy)phenyl)acrylamide |
| "A68" | 1-(3-(((6-amino-5-(4-phenoxyphenyl)pyrimidin-4-yl)amino)methyl)-8-azabicyclo[3.2.1]octan-8-yl)prop-2-yn-1-one |
| "A69" | N-(3-((6-amino-5-(1-(4-cyanobenzyl)-1H-pyrazol-4-yl)pyrimidin-4-yl)oxy)phenyl)acrylamide |
| "A70" | N-(3-((6-amino-5-(1-benzyl-1H-pyrazol-4-yl)pyrimidin-4-yl)amino)phenyl)acrylamide |
| "A71" | (E)-1-(3-(((6-amino-5-(4-phenoxyphenyl)pyrimidin-4-yl)amino)methyl)-8-azabicyclo[3.2.1]octan-8-yl)-4-(dimethylamino)but-2-en-1-one |
| "A72" | N-(3-((6-amino-5-(1-(4-methoxybenzyl)-1H-pyrazol-4-yl)pyrimidin-4-yl)oxy)phenyl)acrylamide |
| "A73" | (R,E)-1-(3-((6-amino-5-(4-phenoxyphenyl)pyrimidin-4-yl)amino)pyrrolidin-1-yl)-4-(dimethylamino)but-2-en-1-one |
| "A74" | (R,E)-1-(3-((6-amino-5-(4-phenoxyphenyl)pyrimidin-4-yl)amino)piperidin-1-yl)-4-(dimethylamino)but-2-en-1-one |
| "A75" | 1-(trans-3-((6-amino-5-(4-phenoxyphenyl)pyrimidin-4-yl)amino)-4-hydroxypyrrolidin-1-yl)prop-2-en-1-one |
| "A76" | 1-(4-(((2-amino-3-(4-phenoxyphenyl)pyridin-4-yl)amino)methyl)piperidin-1-yl)prop-2-en-1-one |
| "A77" | 1-(4-(((6-amino-5-(4-fluorophenyl)pyrimidin-4-yl)amino)methyl)piperidin-1-yl)prop-2-en-1-one |
| "A78" | 1-(4-(((6-amino-5-(4-(trifluoromethoxy)phenyl)pyrimidin-4-yl)amino)methyl)piperidin-1-yl)prop-2-en-1-one |
| "A79" | 1-(4-(((6-amino-5-(4-(trifluoromethyl)phenoxy)phenyl)pyrimidin-4-yl)amino)methyl)piperidin-1-yl)prop-2-en-1-one |
| "A80" | 1-(4-(((6-amino-5-(4-(4-(fluorophenoxy)phenyl)pyrimidin-4-yl)amino)methyl)piperidin-1-yl)prop-2-en-1-one |
| "A81" | 1-(4-(((6-amino-5-(4-(trifluoromethyl)phenyl)pyrimidin-4-yl)amino)methyl)piperidin-1-yl)prop-2-en-1-one |
| "A82" | 1-(4-(((6-amino-5-(3,4-dimethoxyphenyl)pyrimidin-4-yl)amino)methyl)piperidin-1-yl)prop-2-en-1-one |
| "A83" | 1-(4-(((6-amino-5-(3,4,5-trimethoxyphenyl)pyrimidin-4-yl)amino)methyl)piperidin-1-yl)prop-2-en-1-one |
| "A84" | 1-(4-(((6-amino-5-(2,3-dihydrobenzo[b][1,4]dioxin-6-yl)pyrimidin-4-yl)amino)methyl)piperidin-1-yl)prop-2-en-1-one |
| "A85" | 1-(4-(((6-amino-5-(4-methoxyphenyl)pyrimidin-4-yl)amino)methyl)piperidin-1-yl)prop-2-en-1-one |
| "A86" | 4-(4-(4-(((1-acryloylpiperidin-4-yl)methyl)amino)-6-aminopyrimidin-5-yl)phenoxy)benzonitrile |
| "A87" | 1-(4-(((6-amino-5-(2,5-difluoro-4-phenoxyphenyl)pyrimidin-4-yl)amino)methyl)piperidin-1-yl)prop-2-en-1-one |
| "A88" | 1-(4-(((6-amino-5-(2,3-difluoro-4-phenoxyphenyl)pyrimidin-4-yl)amino)methyl)piperidin-1-yl)prop-2-en-1-one |
| "A89" | 1-(4-(((6-amino-5-(4-((1-methylpiperidin-4-yl)oxy)phenyl)pyrimidin-4-yl)amino)methyl)piperidin-1-yl)prop-2-en-1-one |
| "A90" | 1-(4-(((6-amino-5-(4-phenoxy-2-(trifluoromethyl)phenyl)pyrimidin-4-yl)amino)methyl)piperidin-1-yl)prop-2-en-1-one |
| "A91" | 1-(2-(6-amino-5-(4-phenoxyphenyl)pyrimidin-4-yl)-2,7-diazaspiro[3.5]nonan-7-yl)prop-2-en-1-one |
| "A92" | 1-(8-(6-amino-5-(4-phenoxyphenyl)pyrimidin-4-yl)-2,8-diazaspiro[4.5]decan-2-yl)prop-2-en-1-one |
| "A93" | 1-(7-(6-amino-5-(4-phenoxyphenyl)pyrimidin-4-yl)-2,7-diazaspiro[4.4]nonan-2-yl)prop-2-en-1-one |
| "A94" | 1-(4-(((6-amino-5-(4-(4-hydroxyphenoxy)phenyl)pyrimidin-4-yl)amino)methyl)piperidin-1-yl)prop-2-en-1-one |
| "A95" | 1-(4-(((6-amino-5-(4-(3-(trifluoromethyl)phenoxy)phenyl)pyrimidin-4-yl)amino)methyl)piperidin-1-yl)prop-2-en-1-one |
| "A96" | 1-(4-(((6-amino-5-(4-(pyridin-3-yloxy)phenyl)pyrimidin-4-yl)amino)methyl)piperidin-1-yl)prop-2-en-1-one |
| "A97" | 1-(4-(((6-amino-5-(4-(pyridin-4-yloxy)phenyl)pyrimidin-4-yl)amino)methyl)piperidin-1-yl)prop-2-en-1-one |
| "A98" | 1-(4-(((6-amino-5-(4-(p-tolyloxy)phenyl)pyrimidin-4-yl)amino)methyl)piperidin-1-yl)prop-2-en-1-one |
| "A99" | 1-(4-(((6-amino-5-(4-(cyclohexyloxy)phenyl)pyrimidin-4-yl)amino)methyl)piperidin-1-yl)prop-2-en-1-one |

TABLE 2-continued

| No. | Chemical Name |
|---|---|
| "A100" | N4-((1R,5S,6r)-3-azabicyclo[3.1.0]hexan-6-ylmethyl)-5-(4-phenoxyphenyl)pyrimidine-4,6-diamine hydrochloride |
| "A101" | (3S,4S)-4-(((6-amino-5-(4-phenoxyphenyl)pyrimidin-4-yl)amino)methyl)piperidin-3-ol hydrochloride |
| "A102" | (E)-1-(6-((6-amino-5-chloropyrimidin-4-yl)oxy)-2-azaspiro[3.3]heptan-2-yl)-4-(dimethylamino)but-2-en-1-one |
| "A103" | 1-(3-(2-((6-amino-5-(4-phenoxyphenyl)pyrimidin-4-yl)amino)ethyl)azetidin-1-yl)prop-2-en-1-one |
| "A104" | 1-(3-(2-((6-amino-5-(4-phenoxyphenyl)pyrimidin-4-yl)amino)ethyl)azetidin-1-yl)prop-2-yn-1-one |
| "A105" | (E)-1-(6-((6-amino-5-(4-phenoxyphenyl)pyrimidin-4-yl)oxy)-2-azaspiro[3.3]heptan-2-yl)-4-(dimethylamino)but-2-en-1-one |
| "A106" | 1-(6-((6-amino-5-(1-benzyl-1H-pyrazol-4-yl)pyrimidin-4-yl)oxy)-2-azaspiro[3.3]heptan-2-yl)prop-2-en-1-one |
| "A107" | 1-(6-((6-amino-5-(1-benzyl-1H-pyrazol-4-yl)pyrimidin-4-yl)amino)-2-azaspiro[3.3]heptan-2-yl)prop-2-en-1-one |
| "A108" | 1-(6-((6-amino-5-(4-phenoxyphenyl)pyrimidin-4-yl)amino)-2-azaspiro[3.3]heptan-2-yl)but-2-yn-1-one |
| "A109" | 1-((3S,4S)-4-(((6-amino-5-(1-benzyl-1H-pyrazol-4-yl)pyrimidin-4-yl)amino)methyl)-3-hydroxypiperidin-1-yl)prop-2-en-1-one |
| "A110" | 1-((3S,4S)-4-(((6-amino-5-(1-benzyl-1H-pyrazol-4-yl)pyrimidin-4-yl)amino)methyl)-3-hydroxypiperidin-1-yl)prop-2-yn-1-one |
| "A111" | 1-(6-((6-amino-5-(1-benzyl-1H-pyrazol-4-yl)pyrimidin-4-yl)amino)-2-azaspiro[3.3]heptan-2-yl)prop-2-yn-1-one |
| "A112" | 1-(6-((6-amino-5-(1-benzyl-1H-pyrazol-4-yl)pyrimidin-4-yl)oxy)-2-azaspiro[3.3]heptan-2-yl)prop-2-yn-1-one |
| "A113" | 1-(2-((6-amino-5-(4-phenoxyphenyl)pyrimidin-4-yl)amino)-6-azaspiro[3.4]octan-6-yl)prop-2-en-1-one |
| "A114" | 1-(6-((6-amino-5-(4-(pyridin-4-yloxy)phenyl)pyrimidin-4-yl)oxy)-2-azaspiro[3.3]heptan-2-yl)prop-2-en-1-one |
| "A115" | 1-(2-((6-amino-5-(4-phenoxyphenyl)pyrimidin-4-yl)amino)-6-azaspiro[3.4]octan-6-yl)prop-2-yn-1-one |
| "A116" | 1-(6-((6-amino-5-(1-(pyridin-4-ylmethyl)-1H-pyrazol-4-yl)pyrimidin-4-yl)amino)-2-azaspiro[3.3]heptan-2-yl)prop-2-en-1-one |
| "A117" | N-(1,3-trans-3-((6-amino-5-(4-phenoxyphenyl)pyrimidin-4-yl)amino)cyclobutyl)acrylamide |
| "A118" | N-((1,3-cis-3-((6-amino-5-(4-phenoxyphenyl)pyrimidin-4-yl)amino)cyclobutyl)acrylamide |
| "A119" | N4-(2-(((2-chloroethyl)sulfonyl)-2-azaspiro[3.3]heptan-6-yl)-5-(4-phenoxyphenyl)pyrimidine-4,6-diamine |
| "A120" | 1-(6-((6-amino-5-(4-phenoxyphenyl)pyrimidin-4-yl)oxy)-2-azaspiro[3.3]heptan-2-yl) prop-2-en-1-one |
| "A121" | 1-(4-(((6-amino-5-(4-phenoxyphenyl)pyrimidin-4-yl)amino)methyl)-4-methoxypiperidin-1-yl)prop-2-en-1-one |
| "A122" | N-(6-((6-amino-5-(4-phenoxyphenyl)pyrimidin-4-yl)amino)spiro[3.3]heptan-2-yl)acrylamide |
| "A123" | 1-(1-((6-amino-5-(4-phenoxyphenyl)pyrimidin-4-yl)amino)-7-azaspiro[3.5]nonan-7-yl)prop-2-en-1-one |
| "A124" | 1-(6-((6-amino-5-(4-phenoxyphenyl)pyrimidin-4-yl)amino)-2-azaspiro[3.3]heptan-2-yl)prop-2-en-1-one |
| "A125" | 1-(8-((6-amino-5-(4-phenoxyphenyl)pyrimidin-4-yl)amino)-5-azaspiro[3.5]nonan-5-yl)prop-2-en-1-one |
| "A126" | (E)-1-((3S,4S)-4-(((6-amino-5-(4-phenoxyphenyl)pyrimidin-4-yl)amino)methyl)-3-hydroxypiperidin-1-yl)-4-(dimethylamino)but-2-en-1-one |
| "A127" | (E)-1-(6-((6-amino-5-(4-phenoxyphenyl)pyrimidin-4-yl)amino)-2-azaspiro[3.3]heptan-2-yl)-4-(dimethylamino)but-2-en-1-one |
| "A128" | 3-((6-Amino-5-chloro-pyrimidin-4-ylamino)-methyl)-benzoic acid methyl ester |
| "A129" | Trans-3-(6-Amino-5-chloro-pyrimidin-4-ylamino)-cyclohexanecarboxylic acid methyl ester |
| "A130" | (1R,3S)-3-(6-Amino-5-chloro-pyrimidin-4-ylamino)-cyclohexanecarboxylic acid methyl ester |
| "A131" | 3-((6-Amino-5-(4-phenoxy-phenyl)-pyrimidin-4-ylamino)-methyl)-benzoic acid methyl ester |
| "A132" | Trans-3-(6-amino-5-(4-phenoxyphenyl)-pyrimidin-4-ylamino)-cyclohexanecarboxylic acid methyl ester |
| "A133" | (1R,3S)-3-(6-Amino-5-(4-phenoxyphenyl)-pyrimidin-4-ylamino)-cyclohexanecarboxylic acid methyl ester |
| "A134" | -((6-Amino-5-(4-phenoxy-phenyl)-pyrimidin-4-ylamino)-methyl)-benzoic acid |
| "A135" | (1S,3S)-3-(6-Amino-5-(4-phenoxyphenyl)-pyrimidin-4-ylamino)-cyclohexanecarboxylic acid |
| "A136" | (1R,3S)-3-(6-Amino-5-(4-phenoxyphenyl)-pyrimidin-4-ylamino)-cyclohexanecarboxylic acid |
| "A137" | (4-(6-Amino-5-(4-phenoxyphenyl)-pyrimidin-4-ylamino)-phenyl)-N-methoxy-N-methyl-acetamide |

TABLE 2-continued

| No. | Chemical Name |
|---|---|
| "A138" | 3-((6-Amino-5-(4-phenoxy-phenyl)-pyrimidin-4-ylamino)-methyl)-N-methoxy-N-methyl-benzamide |
| "A139" | (1S,3S)-3-(6-Amino-5-(4-phenoxyphenyl)-pyrimidin-4-ylamino)-cyclohexanecarboxylic acid methoxy-methyl-amide |
| "A140" | (1R,3S)-3-(6-Amino-5-(4-phenoxyphenyl)-pyrimidin-4-ylamino)-cyclohexanecarboxylic acid methoxy-methyl-amide |
| "A141" | 1-(3-((6-Amino-5-(4-phenoxyphenyl)-pyrimidin-4-ylamino)-methyl)-phenyl)-but-2-yn-1-one |
| "A142" | 1-(3-((6-Amino-5-(4-phenoxyphenyl)-pyrimidin-4-ylamino)-methyl)-phenyl)-but-2-en-1-one |
| "A143" | 1-((1S,3S)-3-(6-Amino-5-(4-phenoxyphenyl)-pyrimidin-4-ylamino)-cyclohexyl)-propenone |
| "A144" | 1-((1S,3S)-3-(6-Amino-5-(4-phenoxyphenyl)-pyrimidin-4-ylamino)-cyclohexyl)-but-2-en-1-one |
| "A145" | 1-((1S,3S)-3-(6-Amino-5-(4-phenoxyphenyl)-pyrimidin-4-ylamino)-cyclohexyl)-but-2-yn-1-one |
| "A146" | 1-((1S,3R)-3-(6-Amino-5-(4-phenoxyphenyl)-pyrimidin-4-ylamino)-cyclohexyl)-but-2-en-1-one |
| "A147" | 1-((1S,3R)-3-(6-amino-5-(4-phenoxyphenyl)-pyrimidin-4-ylamino)-cyclohexyl)-but-2-yn-1-one |
| "A148" | (S)-1-(3-((6-amino-5-(4-phenoxyphenyl)pyrimidin-4-yl)amino)pyrrolidin-1-yl)prop-2-en-1-one |
| "A149" | N-(3-((2-amino-3-(4-(benzyloxy)phenyl)pyridin-4-yl)oxy)phenyl)acrylamide |
| "A150" | 1-(3-((2-amino-5-(4-phenoxyphenyl)pyrimidin-4-yl)amino)piperidin-1-yl)prop-2-en-1-one |
| "A151" | (E)-N-(3-((2-amino-3-(4-phenoxyphenyl)pyridin-4-yl)oxy)phenyl)-4-(dimethylamino)but-2-enamide |
| "A152" | (E)-N-(3-((2-amino-3-(4-(benzyloxy)phenyl)pyridin-4-yl)oxy)phenyl)-4-(dimethylamino)but-2-enamide |
| "A153" | (E)-1-(4-(((6-amino-5-(4-phenoxyphenyl)pyrimidin-4-yl)amino)methyl)piperidin-1-yl)-4-(dimethylamino)but-2-en-1-one |
| "A154" | N-cis-4-((6-amino-5-(4-(benzyloxy)phenyl)pyrimidin-4-yl)amino)cyclohexyl)acrylamide |
| "A155" | 4-(4-(((1-acryloylpyrrolidin-3-yl)methyl)amino)-6-aminopyrimidin-5-yl)-N-phenylbenzamide |
| "A156" | 1-(3-(((6-amino-5-(4-(benzyloxy)phenyl)pyrimidin-4-yl)amino)methyl)pyrrolidin-1-yl)prop-2-en-1-one |
| "A157" | 4-(4-(((1-acryloylpiperidin-4-yl)methyl)amino)-6-aminopyrimidin-5-yl)-N-phenylbenzamide |
| "A158" | N-(3-((2-amino-3-(4-phenoxyphenyl)pyridin-4-yl)oxy)-4-fluorophenyl)acrylamide |
| "A159" | 4-(4-((cis-4-acrylamidocyclohexyl)amino)-6-aminopyrimidin-5-yl)-N-phenylbenzamide |
| "A160" | (E)-1-(3-((6-amino-5-(4-phenoxyphenyl)-pyrimidin-4-yl)amino)piperidin-1-yl)-4-(dimethylamino)but-2-en-1-one |
| "A161" | N-(3-((6-amino-5-(6-phenoxypyridin-3-yl)pyrimidin-4-yl)oxy)-4-fluorophenyl)acrylamide |
| "A162" | N-(3-((6-amino-5-(4-(pyridin-2-yloxy)phenyl)pyrimidin-4-yl)oxy)phenyl)acrylamide |
| "A163" | N-(3-((6-amino-5-(3-sulfamoylphenyl)pyrimidin-4-yl)oxy)phenyl)acrylamide |
| "A164" | N-(3-((6-amino-5-(3-(trifluoromethoxy)phenyl)pyrimidin-4-yl)oxy)phenyl)acrylamide |
| "A165" | N-(3-((6-amino-5-(6-(2-fluorophenoxy)pyridin-3-yl)pyrimidin-4-yl)oxy)phenyl)acrylamide |
| "A166" | N-(3-((6-amino-5-(6-(4-fluorophenoxy)pyridin-3-yl)pyrimidin-4-yl)oxy)phenyl)acrylamide |
| "A167" | N-(6-((5-(4-phenoxyphenyl)pyrimidin-4-yl)amino)pyridin-2-yl)acrylamide |
| "A168" | 1-(4-(((6-amino-5-(6-phenoxypyridin-3-yl)pyrimidin-4-yl)amino)methyl)piperidin-1-yl)prop-2-en-1-one |
| "A169" | 1-(4-(((6-amino-5-(4-(3-(trifluoromethyl)phenoxy)phenyl)pyrimidin-4-yl)amino)methyl)-4-hydroxypiperidin-1-yl)prop-2-en-1-one |
| "A170" | 1-((3S,4S)-4-(((6-amino-5-(4-(3-(trifluoromethyl)phenoxy)phenyl)pyrimidin-4-yl)amino)methyl)-3-hydroxypiperidin-1-yl)prop-2-en-1-one |
| "A171" | 1-(4-(((6-amino-2'-phenoxy-[5,5'-bipyrimidin]-4-yl)amino)methyl)piperidin-1-yl)prop-2-en-1-one |
| "A172" | N-(3-((6-amino-5-(1-benzyl-1H-pyrazol-4-yl)pyrimidin-4-yl)oxy)phenyl)acrylamide |
| "A173" | N-((1S,3R)-3-((6-amino-5-(4-phenoxyphenyl)pyrimidin-4-yl)amino)cyclohexyl)acrylamide |
| "A174" | N-((1R,3S)-3-((6-amino-5-(4-phenoxyphenyl)pyrimidin-4-yl)amino)cyclohexyl)acrylamide |
| "A175" | N-((1R,3R)-3-((6-amino-5-(4-phenoxyphenyl)pyrimidin-4-yl)amino)cyclohexyl)acrylamide |

TABLE 2-continued

| No. | Chemical Name |
|---|---|
| "A176" | N-((1S,3S)-3-((6-amino-5-(4-phenoxyphenyl)pyrimidin-4-yl)amino)cyclohexyl)acrylamide |
| "A177" | N-(4-((6-amino-5-(4-phenoxyphenyl)pyrimidin-4-yl)amino)bicyclo[2.1.1]hexan-1-yl)acrylamide |
| "A178" | (R)-N4-(1-((perfluorophenyl)sulfonyl)pyrrolidin-3-yl)-5-(4-phenoxyphenyl)pyrimidine-4,6-diamine |
| "A179" | (R)-N4-(1-((perfluorophenyl)sulfonyl)piperidin-3-yl)-5-(4-phenoxyphenyl)pyrimidine-4,6-diamine |
| "A180" | (R)-1-(3-((6-amino-5-(1-benzyl-1H-pyrazol-4-yl)pyrimidin-4-yl)amino)piperidin-1-yl)prop-2-en-1-one |
| "A181" | N-(cis-3-((6-amino-5-(4-phenoxyphenyl)pyrimidin-4-yl)amino)cyclopentyl)acrylamide |
| "A182" | N-(3-(((6-amino-5-(4-phenoxyphenyl)pyrimidin-4-yl)amino)methyl)cyclobutyl)acrylamide |
| "A183" | N-(3-((6-amino-5-(1-(3,5-difluorobenzyl)-1H-pyrazol-4-yl)pyrimidin-4-yl)oxy)phenyl)acrylamide |
| "A184" | N-(3-((6-amino-5-(1-(2-fluorobenzyl)-1H-pyrazol-4-yl)pyrimidin-4-yl)oxy)phenyl)acrylamide |
| "A185" | 1-(3-((6-amino-5-(4-phenoxyphenyl)pyrimidin-4-yl)amino)azetidin-1-yl)prop-2-en-1-one |
| "A186" | N-(5-((6-amino-5-(4-phenoxyphenyl)pyrimidin-4-yl)amino)pyridin-3-yl)acrylamide |
| "A187" | N-(3-((6-amino-5-(1-(4-fluorobenzyl)-1H-pyrazol-4-yl)pyrimidin-4-yl)oxy)phenyl)acrylamide |
| "A188" | N-((1R,3S,5R)-3-((6-amino-5-(4-phenoxyphenyl)pyrimidin-4-yl)amino)-5-hydroxycyclohexyl)acrylamide (racemic) |
| "A189" | N-(5-((6-amino-5-(1-benzyl-1H-pyrazol-4-yl)pyrimidin-4-yl)oxy)pyridin-3-yl)acrylamide |
| "A190" | N-(3-((6-amino-5-(1-(3-methylbenzyl)-1H-pyrazol-4-yl)pyrimidin-4-yl)oxy)phenyl)acrylamide |
| "A191" | N-(3-((6-amino-5-(1-(3-chlorobenzyl)-1H-pyrazol-4-yl)pyrimidin-4-yl)oxy)phenyl)acrylamide |
| "A192" | (R)-1-(2-(((6-amino-5-(1-benzyl-1H-pyrazol-4-yl)pyrimidin-4-yl)oxy)methyl)morpholino)prop-2-en-1-one |
| "A193" | (S)-1-(2-(((6-amino-5-(1-benzyl-1H-pyrazol-4-yl)pyrimidin-4-yl)oxy)methyl)morpholino)prop-2-en-1-one |
| "A194" | N-(3-((6-amino-5-(1-(2-cyanobenzyl)-1H-pyrazol-4-yl)pyrimidin-4-yl)oxy)phenyl)acrylamide |
| "A195" | N-(3-((6-amino-5-(1-(3-(trifluoromethyl)benzyl)-1H-pyrazol-4-yl)pyrimidin-4-yl)oxy)phenyl)acrylamide |
| "A196" | (R)-1-(3-(((6-amino-5-(1-benzyl-1H-pyrazol-4-yl)pyrimidin-4-yl)oxy)methyl)pyrrolidin-1-yl)prop-2-en-1-one |
| "A197" | N-(5-((6-amino-5-(4-(4-cyanophenoxy)phenyl)pyrimidin-4-yl)oxy)pyridin-3-yl)acrylamide |
| "A198" | N-(3-((6-amino-5-(1-(3-methoxybenzyl)-1H-pyrazol-4-yl)pyrimidin-4-yl)oxy)phenyl)acrylamide |
| "A199" | 4-(4-(((((3S,4S)-1-acryloyl-3-hydroxypiperidin-4-yl)methyl)amino)-6-aminopyrimidin-5-yl)phenoxy)benzonitrile |
| "A200" | (R)-4-(4-(4-((4-acryloylmorpholin-2-yl)methoxy)-6-aminopyrimidin-5-yl)phenoxy)benzonitrile |
| "A201" | (R)-4-(4-(4-((1-acryloylpyrrolidin-3-yl)methoxy)-6-aminopyrimidin-5-yl)phenoxy)benzonitrile |
| "A202" | 4-(4-(4-((2-acryloyl-azaspiro[3.3]heptan-6-yl)oxy)-6-aminopyrimidin-5-yl)phenoxy)benzonitrile |
| "A203" | N-(3-((6-amino-5-(1-(3-cyanobenzyl)-1H-pyrazol-4-yl)pyrimidin-4-yl)oxy)phenyl)acrylamide |
| "A204" | 1-((3S,5S)-3-((6-amino-5-(4-phenoxyphenyl)pyrimidin-4-yl)amino)-5-fluoropiperidin-1-yl)prop-2-en-1-one |
| "A205" | 1-((3R,5R)-3-((6-amino-5-(4-phenoxyphenyl)pyrimidin-4-yl)amino)-5-fluoropiperidin-1-yl)prop-2-en-1-one |
| "A206" | methyl 3-((4-(4-(3-acrylamidophenoxy)-6-aminopyrimidin-5-yl)-1H-pyrazol-1-yl)methyl)benzoate |
| "A207" | 4-(4-(4-((2-acryloyl-2-azaspiro[3.3]heptan-6-yl)amino)-6-aminopyrimidin-5-yl)phenoxy)benzonitrile |
| "A208" | 4-(4-(4-(((8-acryloyl-8-azabicyclo[3.2.1]octan-3-yl)methyl)amino)-6-aminopyrimidin-5-yl)phenoxy)benzonitrile |
| "A209" | 1-(3-(((6-amino-5-(1-benzyl-1H-pyrazol-4-yl)pyrimidin-4-yl)amino)methyl)-8-azabicyclo[3.2.1]octan-8-yl)prop-2-en-1-one |
| "A210" | 1-((3R,4R)-3-((6-amino-5-(4-phenoxyphenyl)pyrimidin-4-yl)amino)-4-hydroxypiperidin-1-yl)prop-2-en-1-one (racemic) |
| "A211" | N-(3-((6-amino-5-(1-(3-(methylsulfonyl)benzyl)-1H-pyrazol-4-yl)pyrimidin-4-yl)oxy)phenyl)acrylamide |
| "A212" | N-(3-((6-amino-5-(1-(3-(dimethylamino)benzyl)-1H-pyrazol-4-yl)pyrimidin-4-yl)oxy)phenyl)acrylamide |
| "A213" | N-(3-((6-amino-5-(4-(3-cyanophenoxy)phenyl)pyrimidin-4-yl)oxy)phenyl)acrylamide |
| "A214" | 3-(4-(4-(((1-acryloylpiperidin-4-yl)methyl)amino)-6-aminopyrimidin-5-yl)phenoxy)benzonitrile |

TABLE 2-continued

| No. | Chemical Name |
|---|---|
| "A215" | 1-((3S,4S)-4-(((6-amino-5-(4-phenoxyphenyl)pyrimidin-4-yl)amino)methyl)-3-hydroxypiperidin-1-yl)but-2-yn-1-one |
| "A216" | 1-acryloyl-4-(((6-amino-5-(4-phenoxyphenyl)pyrimidin-4-yl)amino)methyl)piperidine-4-carboxylic acid |
| "A217" | (E)-4-(((6-amino-5-(4-phenoxyphenyl)pyrimidin-4-yl)amino)methyl)-1-(4-(dimethylamino)but-2-enoyl)piperidine-4-carboxylic acid |
| "A218" | (E)-1-(4-(((6-amino-5-(4-phenoxyphenyl)pyrimidin-4-yl)amino)methyl)piperidin-1-yl)-4-(3-fluoroazetidin-1-yl)but-2-en-1-one |
| "A219" | (E)-1-(4-(((6-amino-5-(4-phenoxyphenyl)pyrimidin-4-yl)amino)methyl)piperidin-1-yl)-4-(3,3-difluoroazetidin-1-yl)but-2-en-1-one |
| "A220" | (E)-1-(4-(((6-amino-5-(4-phenoxyphenyl)pyrimidin-4-yl)amino)methyl)piperidin-1-yl)-4-(pyrrolidin-1-yl)but-2-en-1-one |
| "A221" | 1-(6-((6-amino-5-(4-(pyridin-3-yloxy)phenyl)pyrimidin-4-yl)oxy)-2-azaspiro[3.3]heptan-2-yl)prop-2-en-1-one |
| "A222" | (E)-1-(6-((6-amino-5-(4-phenoxyphenyl)pyrimidin-4-yl)oxy)-2-azaspiro[3.3]heptan-2-yl)-4-(3-fluoroazetidin-1-yl)but-2-en-1-one |
| "A223" | (E)-1-(6-((6-amino-5-(4-phenoxyphenyl)pyrimidin-4-yl)oxy)-2-azaspiro[3.3]heptan-2-yl)-4-(3-fluoroazetidin-1-yl)but-2-en-1-one |
| "A224" | (E)-N-(1,3-cis-3-((6-amino-5-(4-phenoxyphenyl)pyrimidin-4-yl)amino)cyclobutyl)-4-(dimethylamino)but-2-enamide |
| "A225" | 1-(4-(((6-amino-5-(4-phenoxyphenyl)pyrimidin-4-yl)amino)methyl)-4-fluoropiperidin-1-yl)prop-2-en-1-one (2) |
| "A226" | (E)-1-(2-((6-amino-5-(4-phenoxyphenyl)pyrimidin-4-yl)amino)-6-azaspiro[3.4]octan-6-yl)-4-(dimethylamino)but-2-en-1-one |
| "A227" | (E)-1-(4-(((6-amino-5-(4-phenoxyphenyl)pyrimidin-4-yl)amino)methyl)-4-fluoropiperidin-1-yl)-4-(dimethylamino)but-2-en-1-one |
| "A228" | (E)-N-(1,3-trans-3-((6-amino-5-(4-phenoxyphenyl)pyrimidin-4-yl)amino)cyclobutyl)-4-(dimethylamino)but-2-enamide |
| "A229" | N-(1,3-cis-3-((6-amino-5-(1-benzyl-1H-pyrazol-4-yl)pyrimidin-4-yl)amino)cyclobutyl)acrylamide |
| "A230" | (E)-N-(1,3-cis-3-((6-amino-5-(1-benzyl-1H-pyrazol-4-yl)pyrimidin-4-yl)amino)cyclobutyl)-4-(dimethylamino)but-2-enamide |
| "A231" | (E)-1-(4-(((6-amino-5-(4-phenoxyphenyl)pyrimidin-4-yl)amino)methyl)piperidin-1-yl)-3-phenylprop-2-en-1-one |
| "A232" | 1-((3S,4S)-4-(((6-amino-5-(4-phenoxyphenyl)pyrimidin-4-yl)amino)methyl)-3-hydroxypiperidin-1-yl)-3-(dimethylamino)propan-1-one |
| "A233" | 1-((3S,4S)-4-(((6-amino-5-(4-phenoxyphenyl)pyrimidin-4-yl)amino)methyl)-3-hydroxypiperidin-1-yl)-3-(piperidin-1-yl)propan-1-one |
| "A234" | 1-((3S,4S)-4-(((6-amino-5-(4-phenoxyphenyl)pyrimidin-4-yl)amino)methyl)-3-hydroxypiperidin-1-yl)-3-morpholinopropan-1-one |
| "A235" | 1-(4-(((6-amino-5-(4-phenoxyphenyl)pyrimidin-4-yl)amino)methyl)-4-fluoropiperidin-1-yl)-3-(piperidin-1-yl)propan-1-one |
| "A236" | (E)-N-(1,3-cis-3-((6-amino-5-(4-(3-(trifluoromethyl)phenoxy)phenyl)pyrimidin-4-yl)amino)cyclobutyl)-4-(dimethylamino)but-2-enamide |
| "A237" | N-(1,3-trans-3-((6-amino-5-(4-(3-(trifluoromethyl)phenoxy)phenyl)pyrimidin-4-yl)amino)cyclobutyl)acrylamide |
| "A238" | N-(1,3-cis-3-((6-amino-5-(4-(3-(trifluoromethyl)phenoxy)phenyl)pyrimidin-4-yl)amino)cyclobutyl)acrylamide |
| "A239" | 1-acryloyl-4-(((6-amino-5-(4-(3-(trifluoromethyl)phenoxy)phenyl)pyrimidin-4-yl)amino)methyl)piperidine-4-carboxylic acid |
| "A240" | N-(3-((6-amino-5-(4-phenoxyphenyl)pyrimidin-4-yl)oxy)-2-fluorophenyl)acrylamide |
| "A241" | N-(3-(4-amino-6-((4-phenoxyphenyl)amino)pyrimidin-5-yl)phenyl)acrylamide |
| "A242" | N-(3-((6-amino-5-(4-phenoxyphenyl)pyrimidin-4-yl)oxy)phenyl)acrylamide |
| "A243" | N-(3-(2-amino-4-(4-phenoxyphenoxy)pyridin-3-yl)phenyl)acrylamide |
| "A244" | N-(3-((2-amino-3-(4-phenoxyphenyl)pyridin-4-yl)oxy)phenyl)acrylamide |
| "A245" | N-(3-(4-amino-6-(4-phenoxyphenoxy)pyrimidin-5-yl)phenyl)acrylamide |
| "A246" | N-(3-((6-amino-5-(4-phenoxyphenyl)pyrimidin-4-yl)oxy)-4-fluorophenyl)acrylamide |
| "A247" | (R)-1-(3-((6-amino-5-(4-phenoxyphenyl)pyrimidin-4-yl)amino)piperidin-1-yl)prop-2-en-1-one |

TABLE 2-continued

| No. | Chemical Name |
|---|---|
| "A248" | (E)-N-(3-(4-amino-6-(4-phenoxyphenoxy)pyrimidin-5-yl)phenyl)-4-(dimethylamino)but-2-enamide |
| "A249" | N-(3-((6-amino-5-(4-(benzyloxy)phenyl)pyrimidin-4-yl)oxy)phenyl)acrylamide |
| "A250" | 1-(4-(((6-amino-5-(4-phenoxyphenyl)pyrimidin-4-yl)amino)methyl)piperidin-1-yl)prop-2-en-1-one (1) |
| "A251" | N-(5-((6-amino-5-(4-phenoxyphenyl)pyrimidin-4-yl)oxy)-2,4-difluorophenyl)acrylamide |
| "A252" | (E)-N-(3-((6-amino-5-(4-phenoxyphenyl)pyrimidin-4-yl)oxy)phenyl)-4-(dimethylamino)but-2-enamide |
| "A253" | 1-(3-((6-amino-5-(4-phenoxyphenyl)pyrimidin-4-yl)amino)piperidin-1-yl)prop-2-en-1-one |
| "A254" | N-(3-((6-amino-5-(4-((2-methoxybenzyl)oxy)phenyl)pyrimidin-4-yl)oxy)phenyl)acrylamide |
| "A255" | N-(3-((5-(4-phenoxyphenyl)pyrimidin-4-yl)oxy)phenyl)acrylamide |
| "A256" | N-(3-((6-amino-5-(4-(benzyloxy)-3-methoxyphenyl)pyrimidin-4-yl)oxy)phenyl)acrylamide |
| "A257" | N-(3-((6-amino-5-(4-(benzyloxy)-2,3-difluorophenyl)pyrimidin-4-yl)oxy)phenyl)acrylamide |
| "A258" | 4-(4-(3-acrylamidophenoxy)-6-aminopyrimidin-5-yl)-N-phenylbenzamide |
| "A259" | N-(3-((6-amino-5-(6-(benzyloxy)pyridin-3-yl)pyrimidin-4-yl)oxy)phenyl)acrylamide |
| "A260" | N-(3-((6-amino-5-(4-((3-fluorobenzyl)oxy)phenyl)pyrimidin-4-yl)oxy)phenyl)acrylamide |
| "A261" | N-(3-((6-amino-2'-(benzyloxy)-[5,5'-bipyrimidin]-4-yl)oxy)phenyl)acrylamide |
| "A262" | 1-(3-(((6-amino-5-(4-phenoxyphenyl)pyrimidin-4-yl)amino)methyl)pyrrolidin-1-yl)prop-2-en-1-one |
| "A263" | 1-(4-(4-amino-6-(4-phenoxyphenoxy)pyrimidin-5-yl)-5,6-dihydropyridin-1(2H)-yl)prop-2-en-1-one |
| "A264" | N-(3-((6-amino-5-(4-((4-methoxybenzyl)oxy)phenyl)pyrimidin-4-yl)oxy)phenyl)acrylamide |
| "A265" | (E)-N-(3-((6-amino-5-(4-phenoxyphenyl)pyrimidin-4-yl)oxy)phenyl)-4-morpholinobut-2-enamide |
| "A266" | N-((1s,4s)-4-((6-amino-5-(4-phenoxyphenyl)pyrimidin-4-yl)amino)cyclohexyl)acrylamide |
| "A267" | N-(3-(4-((4-phenoxyphenyl)amino)pyridin-3-yl)phenyl)acrylamide |
| "A268" | N-(3-((6-amino-5-(6-phenoxypyridin-3-yl)pyrimidin-4-yl)oxy)phenyl)acrylamide |
| "A269" | 1-(3-((6-amino-5-(4-(benzyloxy)phenyl)pyrimidin-4-yl)amino)piperidin-1-yl)prop-2-en-1-one |
| "A270" | N-(3-((3-(4-phenoxyphenyl)pyridin-4-yl)oxy)phenyl)acrylamide |
| "A271" | N-(3-((2-amino-5-(4-phenoxyphenyl)pyrimidin-4-yl)oxy)phenyl)acrylamide |
| "A272" | 3-(3-acrylamidophenyl)-4-(4-phenoxyphenoxy)picolinamide |
| "A273" | 1-(3-(4-amino-6-((4-phenoxyphenyl)amino)pyrimidin-5-yl)-5,6-dihydropyridin-1(2H)-yl)prop-2-en-1-one |
| "A274" | (E)-N-(3-(4-amino-6-(4-phenoxyphenoxy)pyrimidin-5-yl)phenyl)-4-morpholinobut-2-enamide |
| "A275" | (S)-1-(3-((6-amino-5-(4-phenoxyphenyl)pyrimidin-4-yl)amino)piperidin-1-yl)prop-2-en-1-one |
| "A276" | N-((1r,4r)-4-((6-amino-5-(4-phenoxyphenyl)pyrimidin-4-yl)amino)cyclohexyl)acrylamide |
| "A277" | N-(3-((6-amino-5-(4-fluoro-3-methoxyphenyl)pyrimidin-4-yl)oxy)phenyl)acrylamide |
| "A278" | N-(3-((6-amino-5-(4-(2-hydroxypropan-2-yl)phenyl)pyrimidin-4-yl)oxy)phenyl)acrylamide |
| "A279" | 1-(3-(4-amino-6-(4-phenoxyphenoxy)pyrimidin-5-yl)-5,6-dihydropyridin-1(2H)-yl)prop-2-en-1-one |
| "A280" | N-(4-((6-amino-5-(4-phenoxyphenyl)pyrimidin-4-yl)oxy)phenyl)acrylamide |
| "A281" | N-(4-(4-(4-phenoxyphenoxy)pyridin-3-yl)phenyl)acrylamide |
| "A282" | (E)-4-(dimethylamino)-N-(3-(4-(4-phenoxyphenoxy)pyridin-3-yl)phenyl)but-2-enamide |
| "A283" | N-(3-(4-((4-phenoxyphenyl)amino)pyrimidin-5-yl)phenyl)acrylamide |
| "A284" | 1-(3-((5-(4-phenoxyphenyl)pyrimidin-4-yl)amino)piperidin-1-yl)prop-2-en-1-one |
| "A285" | N-(3-((6-amino-5-(4-(pyrrolidine-1-carbonyl)phenyl)pyrimidin-4-yl)oxy)phenyl)acrylamide |
| "A286" | 1-(3-(((6-amino-5-(4-phenoxyphenyl)pyrimidin-4-yl)amino)methyl)piperidin-1-yl)prop-2-en-1-one |
| "A287" | N-(4-(4-(4-phenoxyphenoxy)pyridin-3-yl)benzyl)acrylamide |
| "A288" | 1-(4'-(4-phenoxyphenoxy)-5,6-dihydro-[3,3'-bipyridin]-1(2H)-yl)prop-2-en-1-one |
| "A289" | N-(3-((6-amino-5-(4-isopropoxyphenyl)pyrimidin-4-yl)oxy)phenyl)acrylamide |

TABLE 2-continued

| No. | Chemical Name |
|---|---|
| "A290" | (E)-N-(4-((6-amino-5-(4-phenoxyphenyl)pyrimidin-4-yl)oxy)phenyl)-4-(dimethylamino)but-2-enamide |
| "A291" | N-(3-((6-amino-5-(5-methoxypyridin-3-yl)pyrimidin-4-yl)oxy)phenyl)acrylamide |
| "A292" | 1-(4-(((6-amino-5-(4-(benzyloxy)phenyl)pyrimidin-4-yl)amino)methyl)piperidin-1-yl)prop-2-en-1-one |
| "A293" | (E)-4-morpholino-N-(3-(4-phenoxyphenoxy)pyridin-3-yl)phenyl)but-2-enamide |
| "A294" | N-(3-((6-amino-5-(4-(benzyloxy)-2,6-difluorophenyl)pyrimidin-4-yl)oxy)phenyl)acrylamide |
| "A295" | (E)-N-(3-((6-amino-5-(4-phenoxyphenyl)pyrimidin-4-yl)oxy)phenyl)-4-(4-(5-((4S)-2-oxohexahydro-1H-thieno[3,4-d]imidazol-4-yl)pentanoyl)piperazin-1-yl)but-2-enamide |
| "A296" | N-(3-(4-(4-phenoxyphenoxy)pyridin-3-yl)phenyl)but-2-ynamide |
| "A297" | N-(4-((3-(4-phenoxyphenyl)pyridin-4-yl)oxy)phenyl)acrylamide |
| "A298" | N-(1-(6-amino-5-(4-phenoxyphenyl)pyrimidin-4-yl)piperidin-3-yl)acrylamide |
| "A299" | 1-(4-((6-amino-5-(4-phenoxyphenyl)pyrimidin-4-yl)amino)piperidin-1-yl)prop-2-en-1-one |
| "A300" | 3-(3-aminophenyl)-4-(4-phenoxyphenoxy)pyridin-2-amine |
| "A301" | (E)-N-(3-(4-amino-6-(4-phenoxyphenoxy)pyrimidin-5-yl)phenyl)-4-(3,3-difluoropiperidin-1-yl)but-2-enamide |
| "A302" | N-(3-(4-phenoxyphenoxy)pyridin-3-yl)benzyl)acrylamide |
| "A303" | 6-(4-aminophenoxy)-5-(4-phenoxyphenyl)pyrimidin-4-amine |
| "A304" | N-(3-(4-phenoxyphenoxy)pyridin-3-yl)benzyl)but-2-ynamide |
| "A305" | 6-(3-aminophenoxy)-5-(4-phenoxyphenyl)pyrimidin-4-amine |
| "A306" | N-(3-(2-amino-4-(4-phenoxyphenoxy)pyrimidin-5-yl)phenyl)acrylamide |
| "A307" | (E)-N-(3-(4-(4-phenoxyphenoxy)pyridin-3-yl)phenyl)but-2-enamide |
| "A308" | N-(4-((6-amino-5-(4-phenoxyphenyl)pyrimidin-4-yl)oxy)phenyl)propionamide |
| "A309" | N-((1-(6-amino-5-(4-phenoxyphenyl)pyrimidin-4-yl)piperidin-3-yl)methyl)acrylamide |
| "A310" | N-(3-(2-amino-4-(4-phenoxyphenoxy)pyridin-3-yl)phenyl)propionamide |
| "A311" | (R)-N-(3-(4-amino-6-((1-phenylethyl)amino)pyrimidin-5-yl)phenyl)acrylamide |
| "A312" | 3-(4-(4-phenoxyphenoxy)pyridin-3-yl)aniline |
| "A313" | 4-(3-aminophenoxy)-3-(4-phenoxyphenyl)pyridin-2-amine |
| "A314" | 4-(4-phenoxyphenoxy)pyridin-3-yl)aniline |
| "A315" | (4-(4-(4-phenoxyphenoxy)pyridin-3-yl)phenyl)methanamine |
| "A316" | (3-(4-(4-phenoxyphenoxy)pyridin-3-yl)phenyl)methanamine |
| "A317" | 5-(3-aminophenyl)-6-(4-phenoxyphenoxy)pyrimidin-4-amine |
| "A318" | N-(3-((3-(4-phenoxyphenyl)pyridin-4-yl)oxy)phenyl)propionamide |
| "A319" | N-(3-(4-(4-phenoxyphenoxy)pyridin-3-yl)phenyl)propionamide |
| "A320" | N-(4-(4-(4-phenoxyphenoxy)pyridin-3-yl)phenyl)propionamide |
| "A321" | N-(4-((3-(4-phenoxyphenyl)pyridin-4-yl)oxy)phenyl)propionamide |
| "A322" | N-(3-(4-(4-phenoxyphenoxy)pyridin-3-yl)phenyl)methacrylamide |
| "A323" | N-(3-(4-(4-phenoxyphenoxy)pyridin-3-yl)benzyl)propionamide |
| "A324" | N-(4-(4-(4-phenoxyphenoxy)pyridin-3-yl)benzyl)propionamide |
| "A325" | N-(3-(4-amino-6-(4-phenoxyphenoxy)pyrimidin-5-yl)phenyl)propionamide |
| "A326" | N-(3-((6-amino-5-(4-phenoxyphenyl)pyrimidin-4-yl)oxy)phenyl)propionamide |
| "A327" | (E)-N-(3-(4-(4-phenoxyphenoxy)pyridin-3-yl)benzyl)but-2-enamide |
| "A328" | 3-(4-phenoxyphenyl)-4-(3-propionamidophenoxy)picolinamide |
| "A329" | N-(3-((6-amino-5-(4-phenoxyphenyl)pyrimidin-4-yl)oxy)phenyl)-1-cyanocyclopropanecarboxamide |
| "A330" | N-(3-(4-amino-6-(4-phenoxyphenoxy)pyrimidin-5-yl)phenyl)-1-cyanocyclopropanecarboxamide |
| "A331" | (E)-3-(7-((6-amino-5-(4-phenoxyphenyl)pyrimidin-4-yl)oxy)naphthalen-2-yl)-N,N-dimethylacrylamide |
| "A332" | 1-(4-(1-((6-amino-5-(4-phenoxyphenyl)pyrimidin-4-yl)amino)ethyl)piperidin-1-yl)prop-2-en-1-one |
| "A333" | 1-(4-(((6-amino-5-(4-phenoxyphenyl)pyrimidin-4-yl)amino)methyl)piperidin-1-yl)propan-1-one |
| "A334" | 1-(4-(((5-(4-phenoxyphenyl)pyrimidin-4-yl)amino)methyl)piperidin-1-yl)prop-2-en-1-one |
| "A335" | 1-(4-(((6-amino-5-(4-(pyridin-2-yloxy)phenyl)pyrimidin-4-yl)amino)methyl)piperidin-1-yl)prop-2-en-1-one |
| "A336" | 1-(4-(((6-amino-5-(4-phenoxyphenyl)pyrimidin-4-yl)amino)methyl)piperidin-1-yl)but-2-yn-1-one |
| "A337" | N4-((1-(6-chloropyridin-2-yl)piperidin-4-yl)methyl)-5-(4-phenoxyphenyl)pyrimidine-4,6-diamine |
| "A338" | 1-(4-(((6-amino-5-(4-phenoxyphenyl)pyrimidin-4-yl)oxy)methyl)piperidin-1-yl)prop-2-en-1-one |

TABLE 2-continued

| No. | Chemical Name |
|---|---|
| "A339" | N-(3-((6-amino-5-(4-(benzyloxy)-2,5-difluorophenyl)pyrimidin-4-yl)oxy)phenyl)acrylamide |
| "A340" | N-(3-((2-amino-3-(4-phenoxyphenyl)pyridin-4-yl)oxy)phenyl)but-2-ynamide |
| "A341" | (R)-1-(3-((6-amino-5-(4-phenoxyphenyl)pyrimidin-4-yl)amino)pyrrolidin-1-yl)but-2-yn-1-one |
| "A342" | N-{3-[6-Amino-5-(4-phenoxy-phenyl)-pyrimidin-4-yloxy]-phenyl}-2-chloroacetamide |
| "A343" | N-(3-{6-Amino-5-[4-(2-fluoro-benzyloxy)-phenyl]-pyrimidin-4-yloxy}-phenyl)-acrylamide |
| "A344" | N-(3-{6-Amino-5-[4-(4-fluoro-benzyloxy)-phenyl]-pyrimidin-4-yloxy}-phenyl)-acrylamide |
| "A345" | N-(3-{6-Amino-5-[4-(3-fluoro-benzyloxy)-phenyl]-pyrimidin-4-yloxy}-phenyl)-2-chloro-acetamide |
| "A346" | N-{3-[6-Amino-5-(4-benzyloxy-phenyl)-pyrimidin-4-yloxy]-phenyl}-propionamide |
| "A347" | N-{3-[6-Amino-5-(4-benzyloxy-phenyl)-pyrimidin-4-yloxy]-phenyl}-2-chloro-acetamide |
| "A348" | N-{3-[6-Amino-5-(4-benzyloxy-3-fluoro-phenyl)-pyrimidin-4-yloxy]-phenyl}-acrylamide |
| "A349" | N-{3-[6-Amino-5-(4-benzyloxy-2-fluoro-phenyl)-pyrimidin-4-yloxy]-phenyl}-acrylamide |
| "A350" | N-{3-(6-Amino-5-(4-benzyloxy-2-fluoro-phenyl)-pyrimidin-4-yloxy}-phenyl)-2-chloro-acetamide |
| "A351" | N-{3-[6-Amino-5-(4-benzyloxy-3-fluoro-phenyl)-pyrimidin-4-yloxy]-phenyl}-2-chloro-acetamide |
| "A352" | N-{4-[4-(3-Acryloylamino-phenoxy)-6-amino-pyrimidin-5-yl]-phenyl}-benzamide |

In certain embodiments, the invention provides a method for the treatment and/or prophylaxis of multiple sclerosis (MS), including relapsing MS (RMS), relapsing-remitting MS (RRMS), progressive MS (PMS), secondary-progressive MS (SPMS), primary-progressive MS (PPMS), and progressive-relapsing MS (PRMS), comprising administering to a subject a compound selected from:
N-[(1-acryloylpiperidin-4-yl)methyl]-5-(4-phenoxyphenyl) pyrimidine-4,6-diamine (1); and
1-(4-(((6-amino-5-(4-phenoxyphenyl)pyrimidin-4-yl) amino)methyl)-4-fluoropiperidin-1-yl)prop-2-en-1-one (2).

In certain embodiments, the invention provides a method as described above, wherein the compound is N-[(1-acryloylpiperidin-4-yl)methyl]-5-(4-phenoxyphenyl)pyrimidine-4,6-diamine (1).

In certain embodiments, the invention provides a method as described above, wherein the compound is 1-(4-(((6-amino-5-(4-phenoxyphenyl)pyrimidin-4-yl)amino)methyl)-4-fluoropiperidin-1-yl)prop-2-en-1-one (2).

In certain embodiments, the invention provides a method for the treatment and/or prophylaxis of multiple sclerosis (MS), comprising administering to a subject, compound (1).

In certain embodiments, the invention provides a method for the treatment and/or prophylaxis of multiple sclerosis (MS), comprising administering to a subject, compound (2).

In certain embodiments, the invention provides a method for the treatment and/or prophylaxis of relapsing MS (RMS), comprising administering to a subject, compound (1).

In certain embodiments, the invention provides a method for the treatment and/or prophylaxis of relapsing MS (RMS), comprising administering to a subject, compound (2).

In certain embodiments, the invention provides a method for the treatment and/or prophylaxis of relapsing-remitting MS (RRMS), comprising administering to a subject, compound (1).

In certain embodiments, the invention provides a method for the treatment and/or prophylaxis of relapsing-remitting MS (RRMS), comprising administering to a subject, compound (2).

In certain embodiments, the invention provides a method for the treatment and/or prophylaxis of progressive MS (PMS), comprising administering to a subject, compound (1).

In certain embodiments, the invention provides a method for the treatment and/or prophylaxis of progressive MS (PMS), comprising administering to a subject, compound (2).

In certain embodiments, the invention provides a method for the treatment and/or prophylaxis of secondary-progressive MS (SPMS), comprising administering to a subject, compound (1).

In certain embodiments, the invention provides a method for the treatment and/or prophylaxis of secondary-progressive MS (SPMS), comprising administering to a subject, compound (2).

In certain embodiments, the invention provides a method for the treatment and/or prophylaxis of primary-progressive MS (PPMS), comprising administering to a subject, compound (1).

In certain embodiments, the invention provides a method for the treatment and/or prophylaxis of primary-progressive MS (PPMS), comprising administering to a subject, compound (2).

In certain embodiments, the invention provides a method for the treatment and/or prophylaxis of progressive-relapsing MS (PRMS), comprising administering to a subject, compound (1).

In certain embodiments, the invention provides a method for the treatment and/or prophylaxis of progressive-relapsing MS (PRMS), comprising administering to a subject, compound (2).

In general, all residues which occur more than once may be identical or different, i.e. are independent of one another.

Above and below, the residues and parameters have the meanings indicated for Formula (I), Formula (II), Formula (III), Formula (IV) and Formula (V) unless expressly indicated otherwise. Accordingly, the invention relates, in particular, to the compounds of Formula (I), Formula (II), Formula (III), Formula (IV) and Formula (V) in which at least one of the said residues has one of the preferred meanings indicated below.

The term "substituted" preferably relates to the substitution by the above-mentioned substituents, where a plurality of different degrees of substitution are possible, unless indicated otherwise.

All physiologically acceptable salts, derivatives, solvates, solvates of salts, and stereoisomers of these compounds, including mixtures thereof in all ratios, are also in accordance with the invention.

The compounds of the Formula (I), (II), (III), (IV) and (V) may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3. An elegant method for the resolution of racemates containing ester groups (for example acetyl esters) is the use of enzymes, in particular esterases.

It is also contemplated that compounds of Formula (I), Formula (II), Formula (III), Formula (IV) and Formula (V) include isotope-labeled forms thereof. An isotope-labeled form of a compound of Formula (I), Formula (II), Formula (III), Formula (IV) and Formula (V) is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the Formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. It is also contemplated that a compound of the Formula I, a prodrug, thereof or a pharmaceutically acceptable salt of either which contains one or more of the above-mentioned isotopes and/or other iso-topes of other atoms are embodiments of the present invention. An isotope-labeled compound of the Formula I can be used in a number of beneficial ways. For example, an isotope-labeled compound of the Formula I into which, for example, a radioisotope, such as $^3H$ or $^{14}C$, has been incorporated, is suitable for medicament and/or substrate tissue distribution assays. These radioisotopes, i.e. tritium ($^3H$) and carbon-14 ($^{14}C$), are particularly preferred owing to their ease of preparation and excellent detectability. Incorporation of heavier isotopes, for example deuterium ($^2H$), into a compound of the Formula I may have therapeutic advantages owing to the higher metabolic stability of this isotope-labeled compound. Higher metabolic stability translates directly into an increased in vivo half-life or lower dosages, which under some circumstances would represent a preferred embodiment of the present invention. An isotope-labeled compound of the Formula I can adapted to the procedures disclosed in the synthesis schemes and the related description, in the example part and in the preparation part in the present text, replacing a non-isotope-labeled reactant by a readily available isotope-labeled reactant.

In other embodiments it is contemplated that deuterium ($^2H$) may be incorporated into a compound of Formula (I), Formula (II), Formula (III), Formula (IV) and Formula (V). Such deuterated compounds can modify the oxidative metabolism of said deuterated compound by means the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is observed in any compounds of Formula (I), Formula (II), Formula (III), Formula (IV) and Formula (V) susceptible to oxidation, the profile of this compound, in vivo, can be drastically modified and result in improved pharmacokinetic properties.

When discovering and developing therapeutic agents, the person skilled in the art attempts to optimize pharmacokinetic parameters while retaining desirable in vitro properties. It is reasonable to assume that many compounds with poor pharmacokinetic profiles are susceptible to oxidative metabolism. In vitro liver microsomal assays known in the are may provide valuable information on the course of oxidative metabolism of this type, which in turn permits the rational design of deuterated compounds of Formula (I), Formula (II), Formula (III), Formula (IV) and Formula (V) with improved stability through resistance to said oxidative metabolism. Significant improvements in the pharmacokinetic profiles of compounds of the Formula I may thereby be obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

While it is not intended that the present invention be limited to any deuterated motif, the following is an example. A compound of Formula (I), Formula (II), Formula (III), Formula (IV) and Formula (V) which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improve-ment in resistance to oxidative metabolism has improved. In this way, it can be determined that the half-life of the parent compound may be extended by up to 100% as the result of deuterium-hydrogen exchange of this type.

Deuterium-hydrogen exchange in a compound of Formula (I), Formula (II), Formula (III), Formula (IV) and Formula (V) can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other BTK inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition, or pharmaceutically acceptable salt, prodrug or hydrate thereof, and a pharmaceutically acceptable carrier, are for the treatment of multiple scleroris (MS), including relapsing MS (RMS), relapsing-remitting MS (RRMS), progressive MS (PMS), secondary-progressive MS (SPMS), primary-progressive MS (PPMS), and progressive-relapsing MS (PRMS).

The invention also relates to the use of compounds according to the invention for the preparation of a medicament for the treatment of multiple scleroris (MS), including relapsing MS (RMS), relapsing-remitting MS (RRMS), progressive MS (PMS), secondary-progressive MS (SPMS), primary-progressive MS (PPMS), and progressive-relapsing MS (PRMS).

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin.

When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

The invention also relates to a set (kit) consisting of separate packs of a) an effective amount of a compound according to the invention or a physiologically acceptable salt, solvate or prodrug thereof, and b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Experimental Section

Efficacy of (1) in PLP139-151 induced EAE in SJL mice (Relapsing Remitting Mouse Model of MS)

Figure 2:
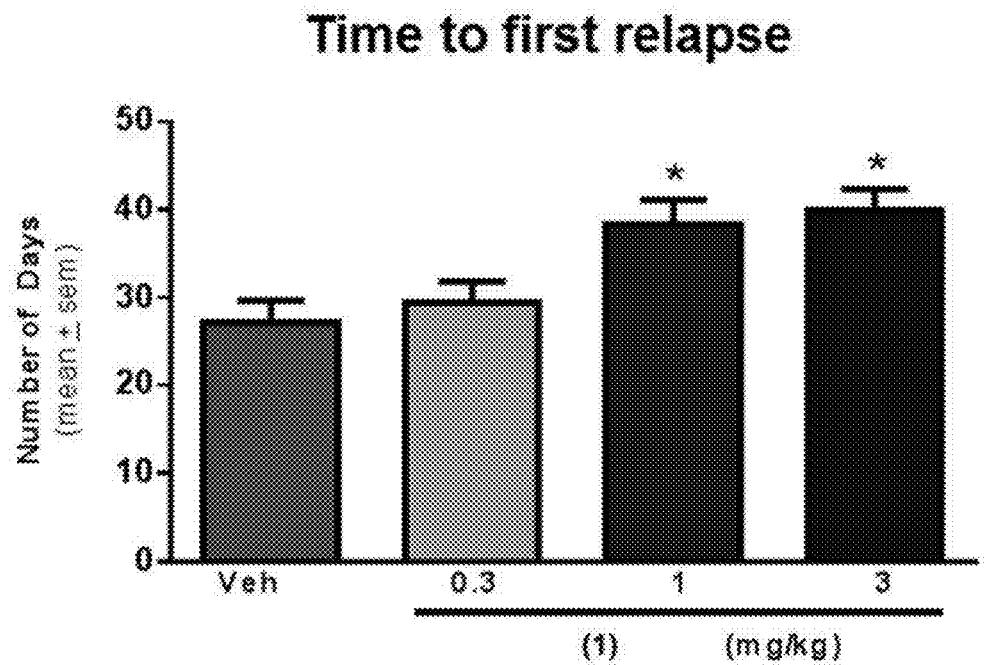
FIG. 2: Prophylactic treatment with (1) reduced relapse activity in SJL-EAE; (a) time to first relapse; (b) total number of relapses; (c) summary.
Figure 2:
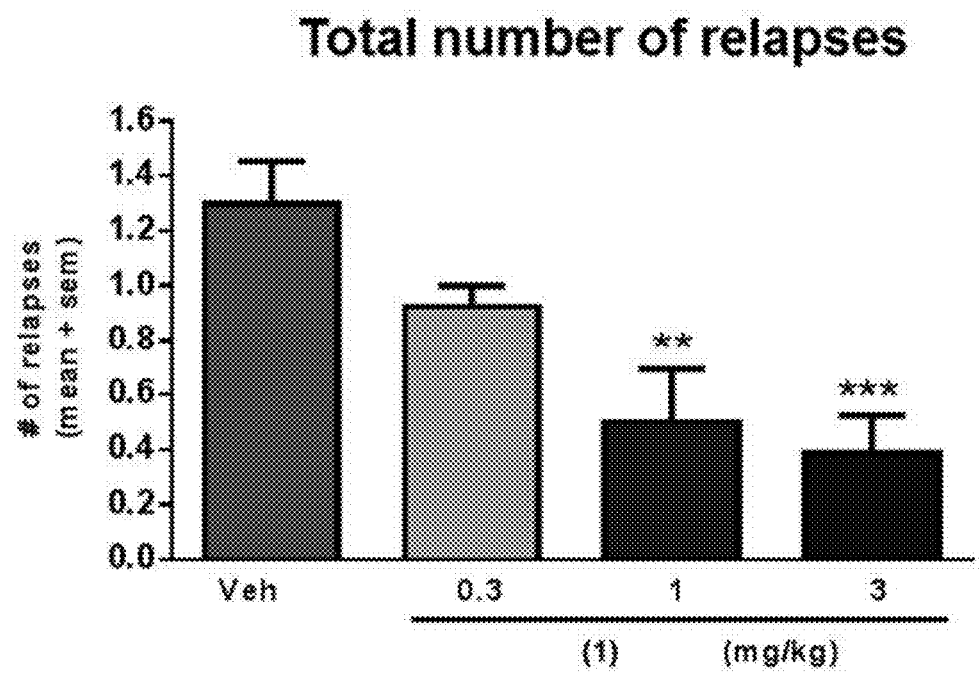

Compound (1) was administered prophylactically in PLP139-151 induced EAE in female SJL mice. Treatment started on Day 0 post-induction: Vehicle, 0.3 mg/kg, 1.0 mg/kg, and 3 mg/kg, and FTY-720 at 3 mg/kg. We also determined PK/PD (receptor occupancy) at first dose and at the end of the study. The results are provided in FIGS. 1 and 2.

Animals: 75 Female SJL mice from Jax (10 weeks at arrival), at least 18 g upon arrival.

Treatment Groups:

| Group | Treatment | Dose | Regimen | Route | N |
|---|---|---|---|---|---|
| A | SHAM | n/a | n/a | n/a | 5 |
| B | Vehicle | n/a | Prophylactic, QD | PO | 15 |
| C | 1 | 0.3 mpk | Prophylactic, QD | PO | 15 |
| D | 1 | 1 mpk | Prophylactic, QD | PO | 15 |
| E | 1 | 3 mpk | Prophylactic, QD | PO | 15 |
| F | FTY-720 | 3 mpk | Prophylactic, QD | PO | 10 |

Solutions Preparation:

CFA Preparation: Total Volume needed: 10 mL; 2 mg/mL of M.T. was added to IFA to get a total concentration of 2 mg/mL M.T. in CFA (Add 100 mg M.T. to 50 mL of IFA).

PLP139-151 Preparation: 100 ug $PLP_{139-151}$: Concentration: 1 mg/mL; 25 mg of PLP in 25 mL PBS. Emulsified PLP/CFA in a 1:1 ratio using homogenizer method.

PTX Preparation: Stock Solution: 1 mL of PBS was added to the vial with 50 ug (store in fridge); 60 ng/mouse (0.2 mL/mouse)=0.3 ug/ml (dilute stock 1:167, 210 ul in 35 mL PBS).

Efficacy of (1) in PLP139-151 induced EAE in SJL mice (BTKi in a Relapsing Remitting Mouse Model of MS—Therapeutic Dosing)

Figures 2, 3:
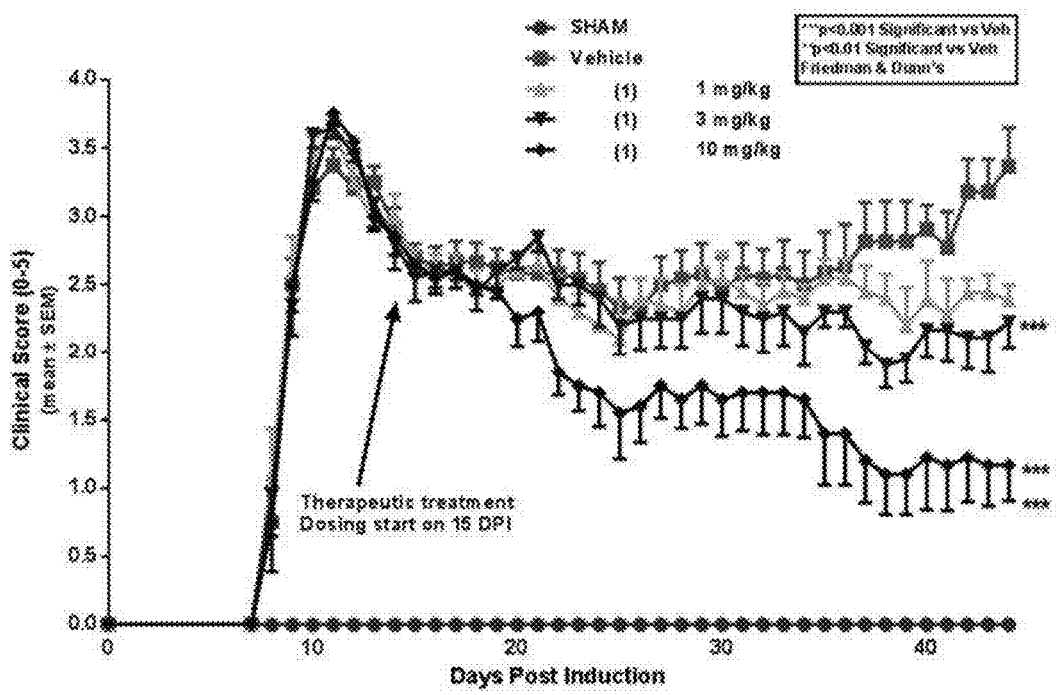
FIG. 3: (a) Therapeutic treatment with (1) reduced disease severity in SJL-EAE; (b) cumulative EAE score.
Figure 3:
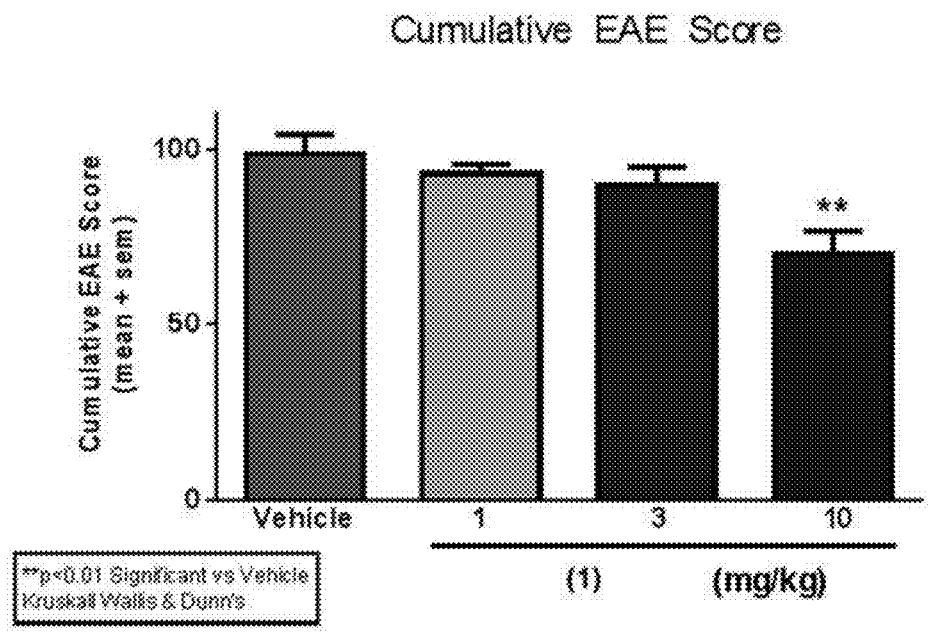
Figure 4:
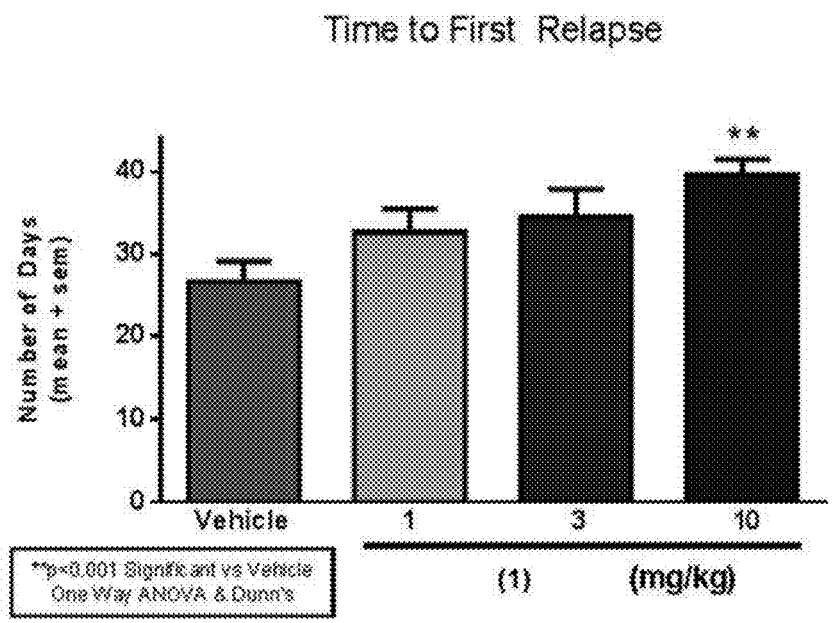
FIG. 4: Therapeutic treatment with (1) reduced relapse activity in SJL-EAE; (a) time to first relapse; (b) total number of relapses; (c) summary.
Figure 4:
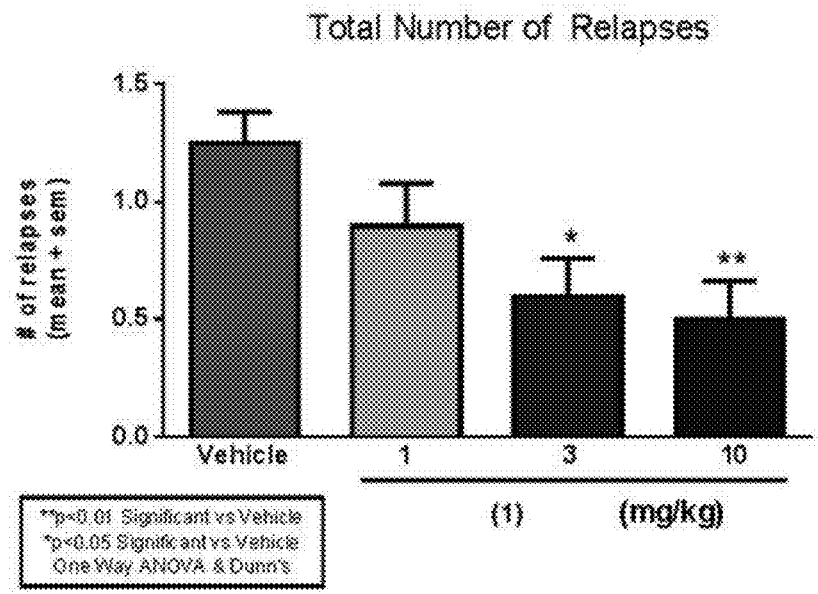
Figure 6:
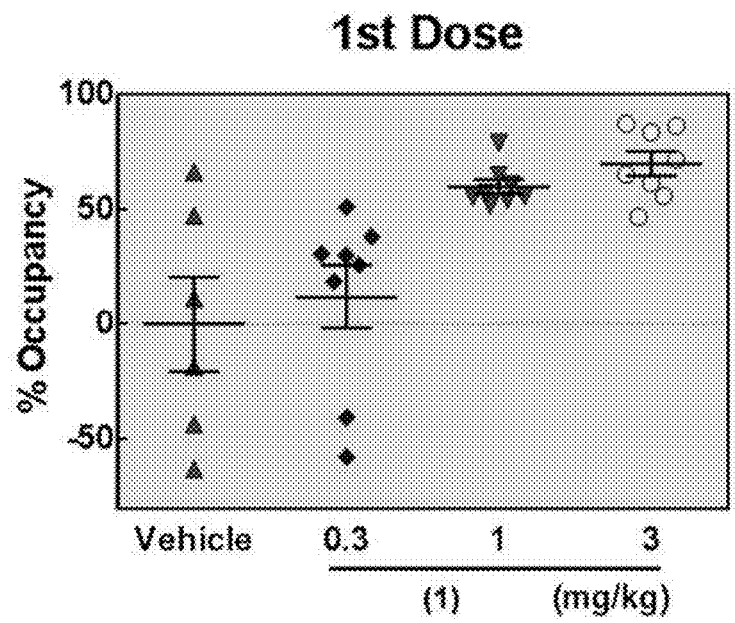
FIG. 6: BTK occupancy after prophylactic treatment with (1) (24 hours post treatment); (a) 1st dose; (b) last dose.
Figure 6:
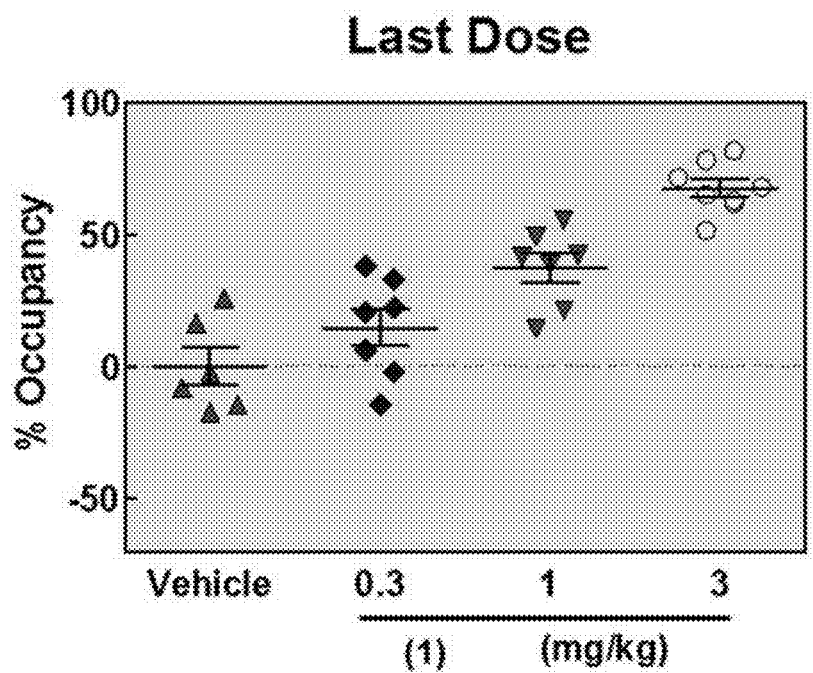
Figure 7:
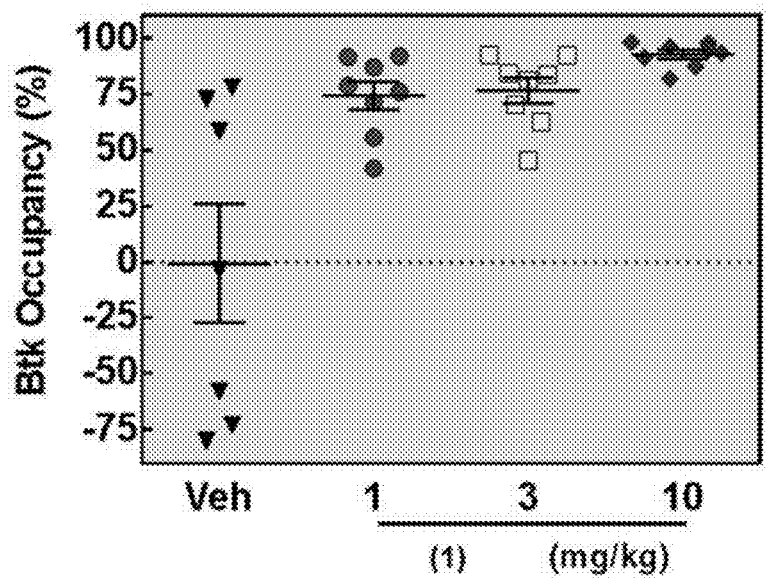
FIG. 7: (a) BTK Occupancy After first (1) Dose (therapeutic study); (b) BTK Blood Concentrations After first (1) Dose (therapeutic study).
Figure 7:
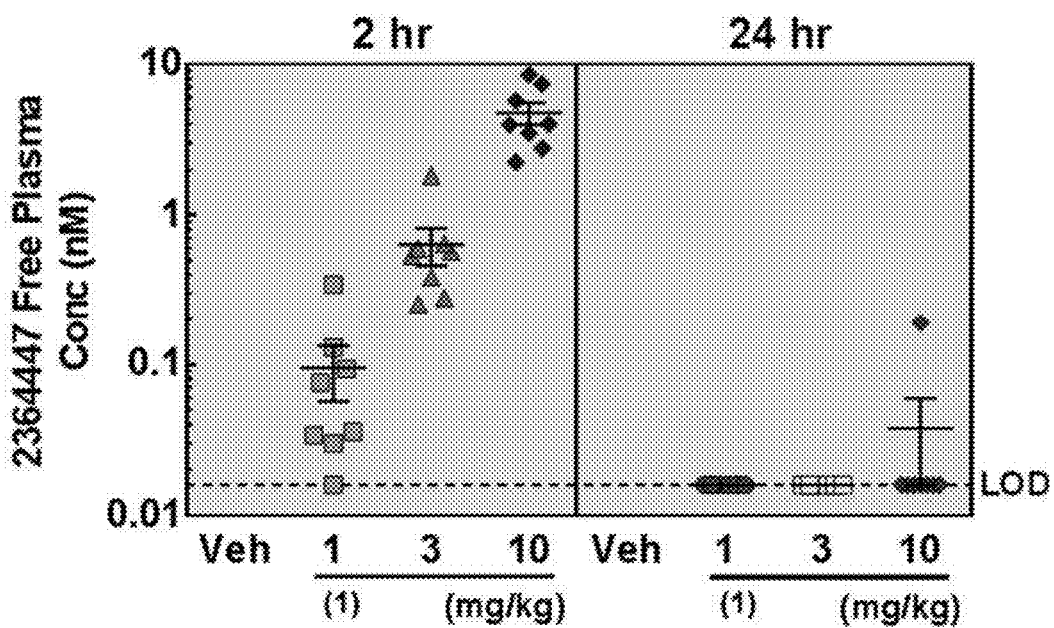
Figure 8:
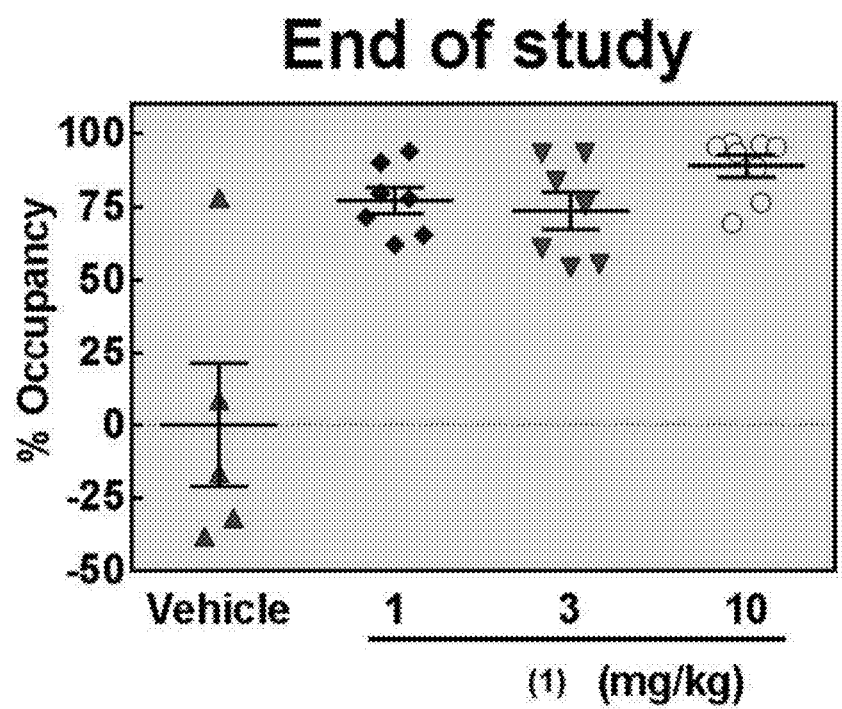
FIG. 8: BTK occupancy after therapeutic treatment with (1) (24 hours post treatment).

Compound (1) was administered in PLP139-151 induced EAE in female SJL mice in both prophylactic (treatment start at induction) and therapeutic (treatment start at remission) dosing regimen. The study was a dose-response: 0.3, 1 and 3 mg/kg for prophylactic dosing regimen and 1, 3 and 10 mg/kg for therapeutic dosing. In addition we determined PK/PD after $1^{st}$ and last dose to enable modeling of efficacy vs receptor occupancy. See FIGS. 3-5.

Animals: 145 Female SJL mice from Jax (10 weeks at arrival), at least 18 g upon arrival.

Treatment Groups:

| Group | Treatment | Dose | Regimen | Route | N |
|---|---|---|---|---|---|
| A | SHAM | n/a | n/a | n/a | 5 |
| B | Vehicle | n/a | Prophylactic, QD | PO | 15 |
| C | (1) | 0.3 mpk | Prophylactic, QD | PO | 15 |
| D | (1) | 1 mpk | Prophylactic, QD | PO | 15 |
| E | (1) | 3 mpk | Prophylactic, QD | PO | 15 |
| F | FTY-720 | 1 mpk | Prophylactic, QD | PO | 10 |
| G | Vehicle | n/a | Therapeutic, QD | PO | 15 |
| H | (1) | 1 mpk | Therapeutic, QD | PO | 15 |
| I | (1) | 3 mpk | Therapeutic, QD | PO | 15 |
| J | (1) | 10 mpk | Therapeutic, QD | PO | 15 |
| K | FTY-720 | 1 mpk | Therapeutic, QD | PO | 10 |

Induction of EAE in SJL Mice:

$PLP_{139-15}$ was dissolved in PBS and emulsified with an equal volume of CFA supplemented with 2 mg/mL *Mycobacterium tuberculosis* (M.T.)(CFA already has 1 mg/ml MT so another 1 mg/ml is added to a final concentration of 2 mg/ml). Mice were injected s.c. with 0.2 ml of peptide emulsion in the abdominal flank (0.1 ml on each side). On the same day and 48 hr later, mice were injected i.p. with 200 µl (60 ng) of *Bordetella Pertussis* toxin in saline.

Solutions Preparation:

CFA Preparation: Total Volume needed: 10 mL; Add 2 mg/mL of M.T. to IFA to get a total concentration of 2 mg/mL M.T. in CFA (add 100 mg M.T. to 50 mL of IFA).

PLP139-151 Preparation: 100 ug $PLP_{139-151}$: Concentration: 1 mg/mL; 25 mg of PLP in 25 mL PBS; PLP/CFA was emulsified in a 1:1 ratio using homogenizer method.

PTX Preparation: Stock Solution: Add 1 mL of PBS to the vial with 50 ug (store in fridge); 60 ng/mouse (0.2 mL/mouse)=0.3 ug/ml (dilute stock 1:167, 210 ul in 35 mL PBS).

BTK Occupancy in Mouse Blood (Compounds 1 and 2)

To calculate the amount of Btk occupancy achieved after dosing with a Btk inhibitor samples were collected from vehicle treated mice. The vehicle group samples were assumed to have 0% occupancy and % occupancy for the Btk inhibitor treated mice was calculated relative to this 0% value. Blood was collected and dispensed into anti-coagulant coated tubes. Either EDTA or heparin were acceptable anti-coagulants. The collected blood was kept at room temperature (20-24 C) until processing. Blood (80 µl) was transferred to a 1.5 ml eppendorf snap cap tube using a pipet. 800 µl of room temperature red blood cell lysis buffer was added, the tube capped, and inverted 3 times to mix. The mixture was incubated for 5 minutes at room temperature. The cells were pelleted by centrifugation for 5 minutes at 600×g at room temperature and then aspirated without disturbing the cell pellet. The cells were washed by resuspending in 400 µl of RBC lysis buffer using a pipet followed by centrifugation for 5 minutes at 600×g (room temperature) and careful aspiration of the liquid. A stock of incubation media was made by combining RPMI1640 and the Btk occupancy probe compound. Media was without any added FBS or Pen/Strep. The probe compound was previously dissolved in DMSO to 10 mM and stored in aliquots at −80 C. 1 µl of 10 mM probe compound per 10 ml of RPMI1640 was added to make the incubation media stock containing a final of 1 µM probe. The pelleted cells were resuspend with 1 ml of incubation media containing the probe. The cells were incubated with the probe for 1 hr at 37 C in a $CO_2$ regulated tissue culture incubator with the tube lids open. The lysis buffer was prepared during the 1 hr incubation (Add 10 µl of HALT protease and phosphatase inhibitor cocktail per ml of MPER lysis buffer. Chill mixed buffer on ice at least 10 minutes before use). After 1 hr incubation, the cells were pelleted by centrifugation at room temperature for 5 minutes at 600×g. The media was aspirated and cells were resuspended in 120 µl of chilled MPER lysis buffer. Incubate on ice after addition of lysis buffer and subsequently store samples at −80 C before usage in the MSD occupancy assay.

The probe:

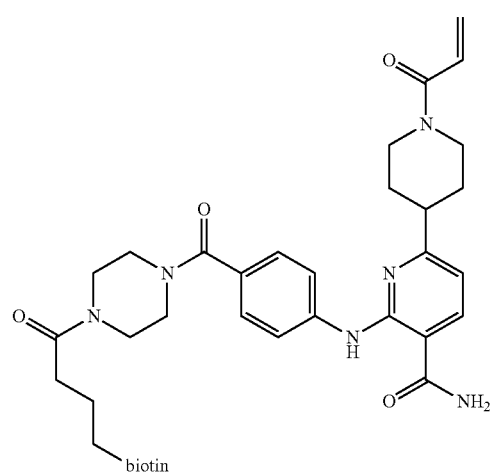

Probe-treated cell lysates were thawed and biotinylated-Btk was quantitated using a streptavidin capture assay performed on the MSD platform. MSD microtiter plates coated with streptavidin were blocked by incubation with 200 µl/well of casein-containing blocking buffer from Pierce for 1 hr. This incubation and all other incubations in the assay were performed at room temperature with gentle shaking at 200 rpm on a microtiter plate shaker and the plate was covered using a plastic adhesive sealer film. After blocking, the plates were washed 1×200 µl/well (PBS/0.05% tween 20). Add 100 µl/well of standards. The cell lysates were diluted (10 µl+200 µl) of blocking buffer in a separate dilution plate prior to addition. 50 µl of diluted cell lysate was added to 50 µl of blocking buffer per well to a final volume of 100 µl/well. It was allowed to incubate for 1.5-2 hr at room temperature. The standards were assayed in duplicate as well as unknown samples. The plate was washed (3×200 µl/well (PBS/0.05% tween 20)) and rabbit anti-Btk antibody was added (100 µl/well) diluted to 1 µg/ml (1:1,000) in blocking buffer. The solution was incubated for 1.5-2 hr at room temp with shaking. The plate was washed (3×200 µl/well (PBS/0.05% tween 20)) and goat anti-rabbit SULFO-tagged antibody was added (100 µl/well) diluted to 1 µg/ml (1:500) in blocking buffer. The solution was incubated for 1.5-2 hr at room temp with shaking. The plate was washed (3×200 µl/well) (PBS/0.05% tween 20), then diluted (4×MSD Read Buffer) to a 2× concentration with water and then added 150 µl/well. The plate was immediately read using an MSD Sector Imager 600. The data was processed using the MSD Discovery Workbench software program.

A standard curve employing recombinant Btk previously treated with biotinylated probe in vitro was used for quantitation. To generate the stock standard, recombinant Btk was treated in vitro at 2 ng/µl in PBS containing 1 mg/ml BSA with 1 µM of the probe for 1 hr at 37 C and then frozen in aliquots at −80 C.

To generate the standard curve an aliquot of the stock of the recombinant Btk standard was diluted 5 µl+245 µl of blocking buffer. The diluted standard was then further diluted in blocking buffer with serial 1:2 dilutions (70 µl+140 µl of blocking buffer). The standards were prepared in the 96 dilution plate same as the samples. The standard curve values for Btk-biotin range from 40 to 0.02 ng/ml. Curve fitting was performed with a four parameter fit in the MSD Discovery Workbench software program.

The assay described above measures probe binding to Btk where inhibitors have not covalently attached to the active site and therefore detects unoccupied Btk. Thus, samples collected from vehicle treated mice contain cells with totally unoccupied Btk and the amount of Btk-biotin detected in those samples was set to 0% occupancy. Cells from a sample of white blood cells incubated ex vivo with 1 µM (1) for 10 min prior to probe treatment were set as 100% occupancy. The percent occupancy of all samples was calculated relative to the vehicle group value, which was set to 0% occupancy. See FIGS. 6-8, 12, 13, and 17.

Efficacy of (2) in PLP139-151 induced EAE in SJL mice (BTKi in a Relapsing Remitting Mouse Model of MS)

Figure 9:
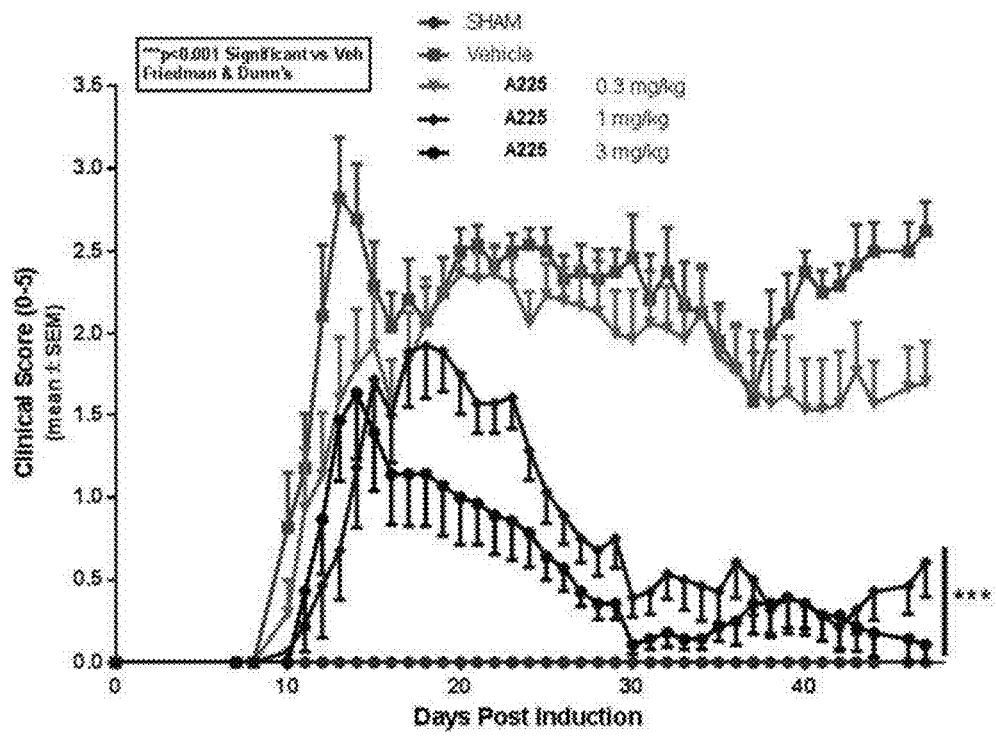
FIG. 9: (a) Compound (2) significantly decreases disease severity when administered prophylactically; (b) cumulative EAE score.
Figure 9:
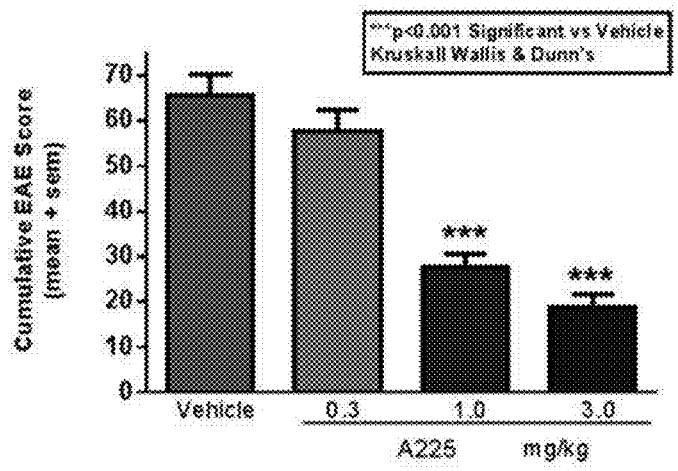
Figure 10:
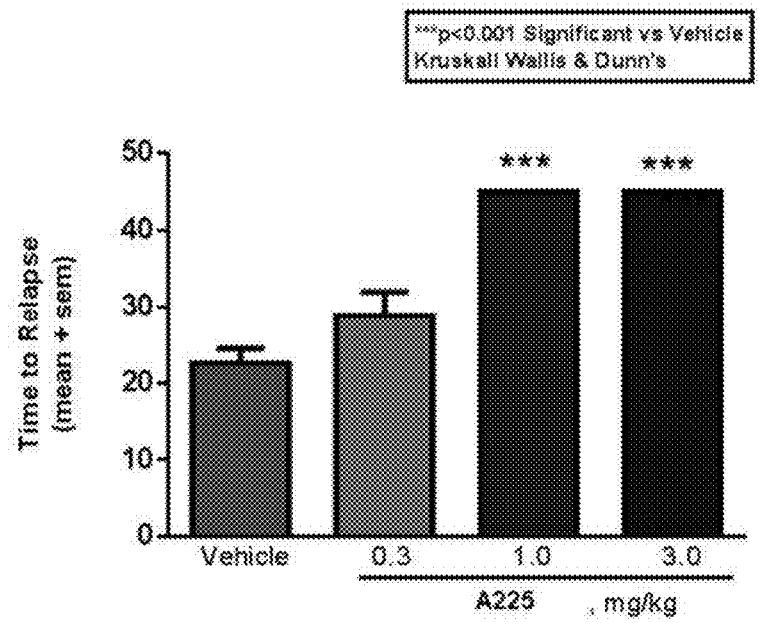
FIG. 10: (a) Compound (2) decreased incidence of disease and relapses in EAE model; (b) summary.
Figure 12:
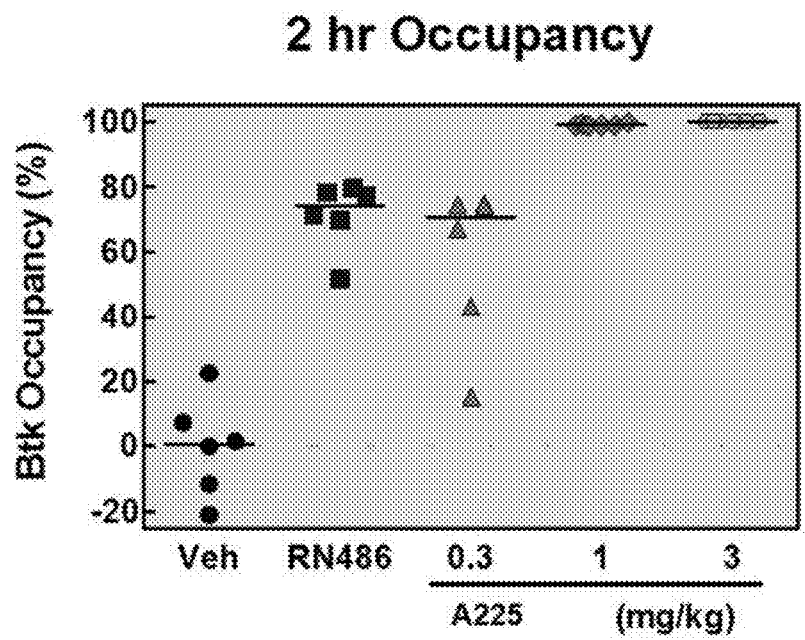
FIG. 12: (a) Compound (2) BTK Occupancy at 2 hr post-dose; (b) Compound (2) BTK Occupancy at 24 hr post-dose (both measured by streptavidin capture MSD assay).
Figure 12:
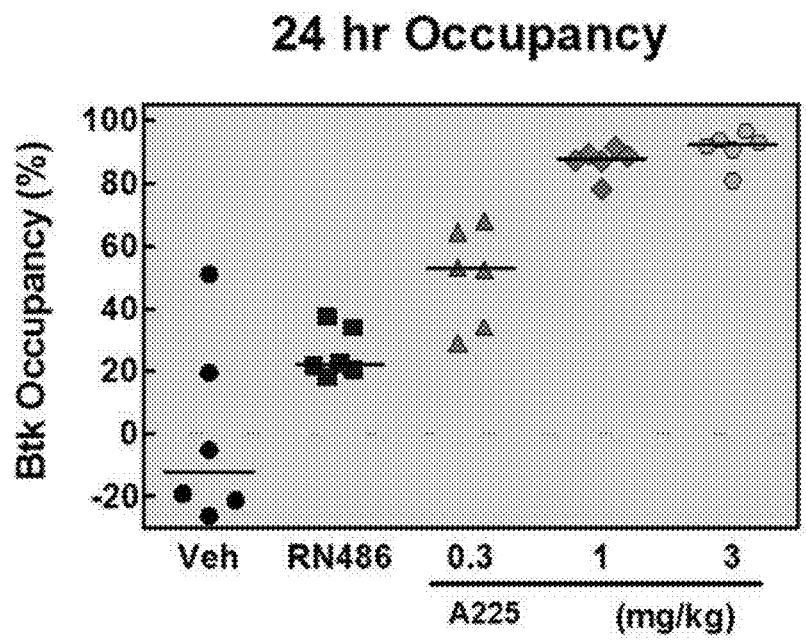
Figure 13:
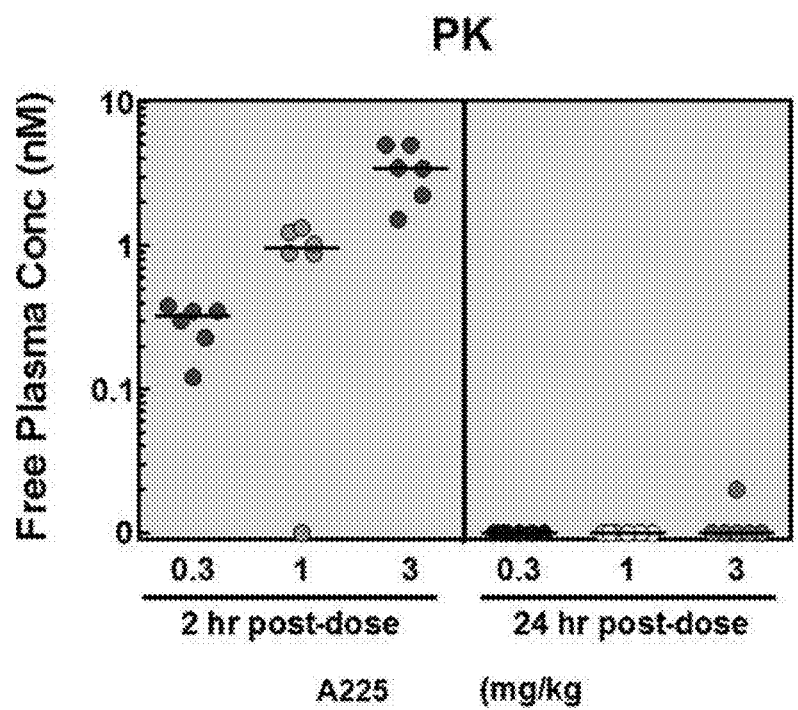
FIG. 13: Compound (2) Free Plasma concentrations at 2 hr and 24 hr post-dose (measured by dried blood spot analysis).

Compound 2 was administered prophylactically (starting day of induction) in PLP139-151 induced EAE in female SJL mice. at 3 mg/kg PO which has been shown in the paper to be efficacious on RA models. Treatment started on Day 0 post-induction: Vehicle, 0.3 mg/kg, 1.0 mg/kg, and 3 mg/kg PO QD. The endpoints included a clinical score and body weight, receptor occupancy and CD69 expression at the end of the study (2 h and 24 h post administration). FIGS. 9-11.

Animals: 90 Female SJL mice from Jax (10 weeks at arrival), at least 18 g upon arrival.

Treatment Groups:

90 mice are induced with PLP/CFA/PTX. Prophylactic treatment starts on the same day as EAE induction (before induction)

| Group | Treatment | Dose | Regimen | Route | N |
|---|---|---|---|---|---|
| A | SHAM | n/a | n/a | n/a | 3 |
| B | Vehicle | n/a | Prophylactic, QD | PO | 15 |
| C | RN486 | 30 mpk | Prophylactic, QD | PO | 15 |
| D | 2 | 0.3 mpk | Prophylactic, QD | PO | 15 |
| E | 2 | 1 mpk | Prophylactic, QD | PO | 15 |
| F | 2 | 3 mpk | Prophylactic, QD | PO | 15 |
| G | FTY-720 | 1 mpk | Prophylactic, QD | PO | 7 |
| H | Anti-CD20 | 250 ug/mouse | Prophylactic (once on Day 0) | IV | 5 |

Induction of EAE in SJL Mice $PLP_{139-15}$ was dissolved in PBS and emulsified with an equal volume of CFA supplemented with 2 mg/mL *Mycobacterium tuberculosis* (M.T.)(CFA already has 1 mg/ml MT so another 1 mg/ml is added to a final concentration of 2 mg/ml). Mice were injected s.c. with 0.2 ml of peptide emulsion in the abdominal flank (0.1 ml on each side). On the same day and 48 hr later, mice were injected i.p. with 200 µl (60 ng) of *Bordetella Pertussis* toxin in saline.

Solutions Preparation:

CFA Preparation: Total Volume needed: 10 mL; 2 mg/mL of M.T. was added to IFA to get a total concentration of 2 mg/mL M.T. in CFA (add 100 mg M.T. to 50 mL of IFA). PLP139-151 Preparation: 100 ug $PLP_{139-151}$: Concentration: 1 mg/mL; 15 mg of PLP in 15 mL PBS. PLP/CFA in a 1:1 ratio was emulsified using homogenizer method.

PTX Preparation: Stock Solution: Add 1 mL of PBS to the vial with 50 ug (store in fridge) 60 ng/mouse (0.2 mL/mouse)=0.3 ug/ml (dilute stock 1:100, 150 ul in 25 mL PBS).

Figure 14:
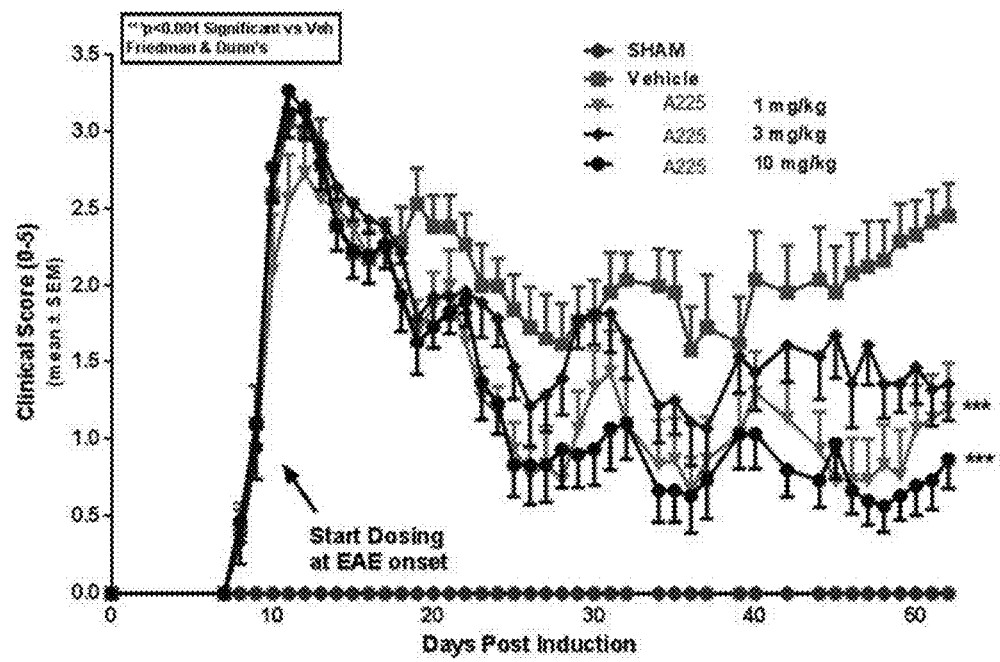
FIG. 14: (a) Therapeutic dosing with Compound (2) reduced disease severity in SJL-EAE; (b) cumulative EAE score.
Figure 14:
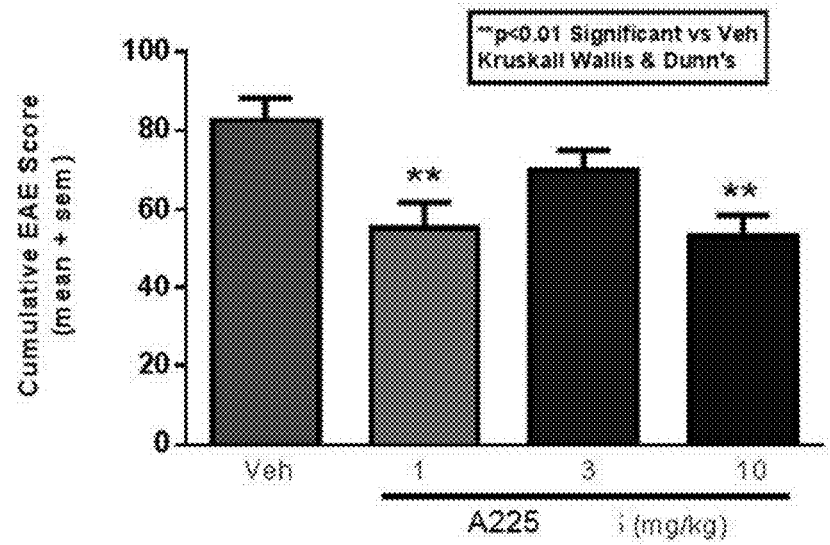
Figure 15:
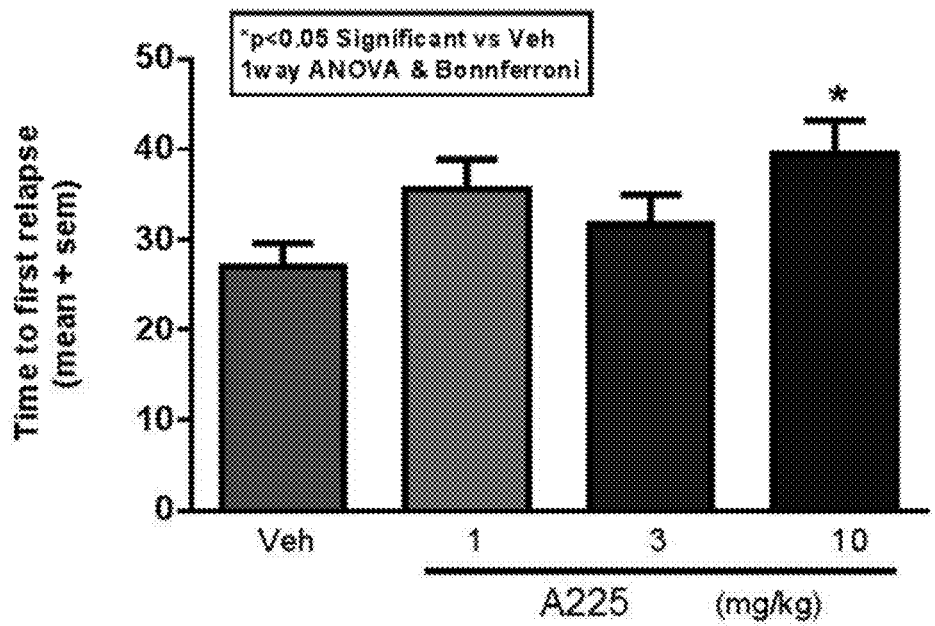
FIG. 15: (a) Therapeutic dosing with Compound (2) prolonged time to first relapse and decreased relapses; (b) number of relapses; (c) summary.
Figure 15:
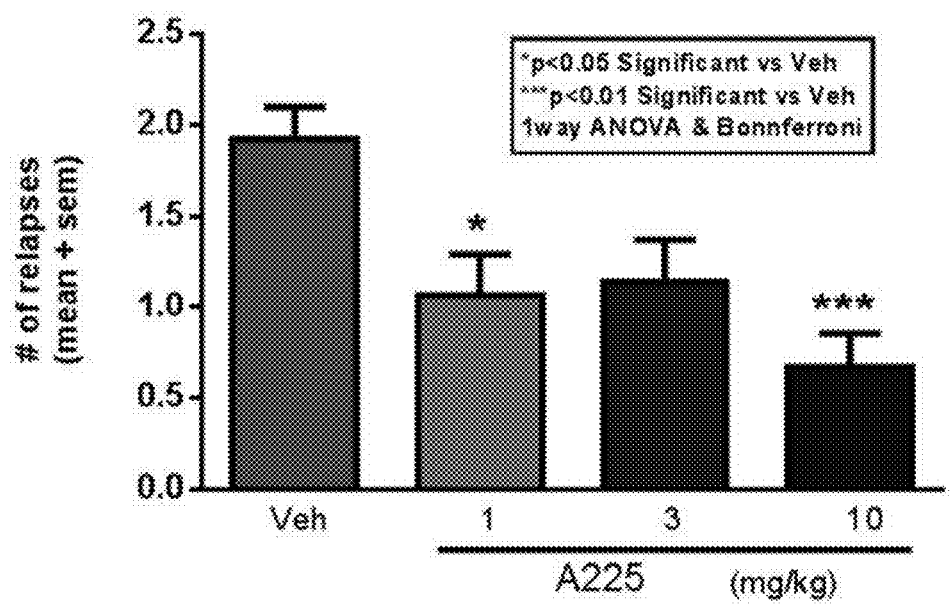
Figure 17:
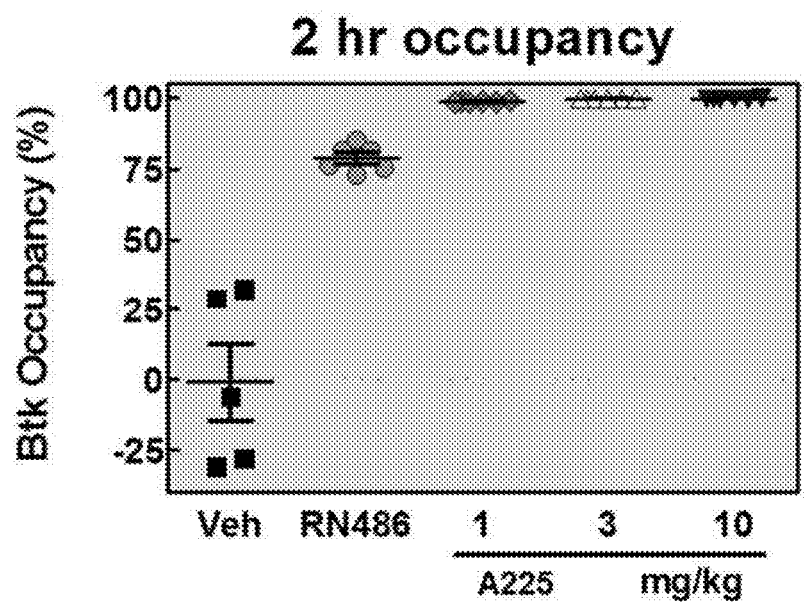
FIG. 17: (a) Compound (2) BTK Occupancy at 2 hr Post-dose; (b) Compound (2) BTK Occupancy at 24 hr Post-dose (measured by streptavidin capture MSD assay).
Figure 17:
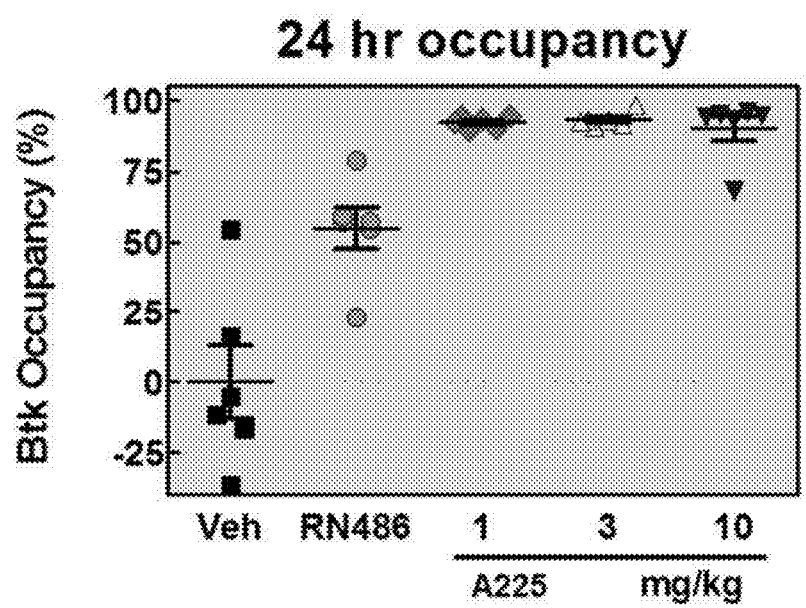

Efficacy of Therapeutic Treatment with BTKi in PLP139-151 induced EAE in SJL Mice Compound 2 was administered therapeutically in PLP139-151 induced EAE in female SJL mice. Dosing began on Day 9 post-induction: Vehicle, 1.0 mg/kg, 3 mg/kg, 10 mg/kg PO QD. The endpoints included a clinical score, receptor occupancy and CD69 expression at the end of the study (2 h and 24 hr post administration). FIGS. 14-16. A B-cell depleting antibody was used as a reference (anti-CD20).

Animals: 100 Female SJL mice from Jax (10 weeks at arrival), at least 18 g upon arrival.

Treatment Groups:

100 mice were induced with PLP/CFA/PTX. At the first signs of disease mice were randomized into different treatment groups according to their clinical score.

| Group | Treatment | Dose | Regimen | Route | N |
|---|---|---|---|---|---|
| A | SHAM | n/a | n/a | n/a | 5 |
| B | Vehicle | n/a | Therapeutic, QD | PO | 15 |
| C | RN486 | 30 mpk | Therapeutic, QD | PO | 15 |
| D | 2 | 1 mpk | Therapeutic, QD | PO | 15 |
| E | 2 | 3 mpk | Therapeutic, QD | PO | 15 |
| F | 2 | 10 mpk | Therapeutic, QD | PO | 15 |
| G | Isotype | 250 ug/mouse | Therapeutic | IV | 10 |
| H | Anti-CD20 | 250 ug/mouse | Therapeutic | IV | 10 |

Induction of EAE in SJL Mice $PLP_{139-151}$ was dissolved in PBS and emulsified with an equal volume of CFA supplemented with 2 mg/mL *Mycobacterium tuberculosis* (M.T.)(CFA already has 1 mg/ml MT so another 1 mg/ml is added to a final concentration of 2 mg/ml). Mice were injected s.c. with 0.2 ml of peptide emulsion in the abdominal flank (0.1 ml on each side). On the same day and 48 hr later, mice were injected i.p. with 200 µl (60 ng) of *Bordetella Pertussis* toxin in saline.

Solutions Preparation:

CFA Preparation: Total Volume needed: 10 mL; Add 2 mg/mL of M.T. to IFA to get a total concentration of 2 mg/mL M.T. in CFA (add 100 mg M.T. to 50 mL of IFA).

PLP139-151 Preparation: 100 ug $PLP_{139-151}$: Concentration: 1 mg/mL; 20 mg of PLP in 20 mL PBS; PLP/CFA was emulsified in a 1:1 ratio using homogenizer method.

PTX Preparation: Stock Solution: Add 1 mL of PBS to the vial with 50 ug (store in fridge) 60 ng/mouse (0.2 mL/mouse)=0.3 ug/ml (dilute stock 1:100, 150 ul in 25 mL PBS).

PLP Induced EAE in SJL Mice

Figure 18:
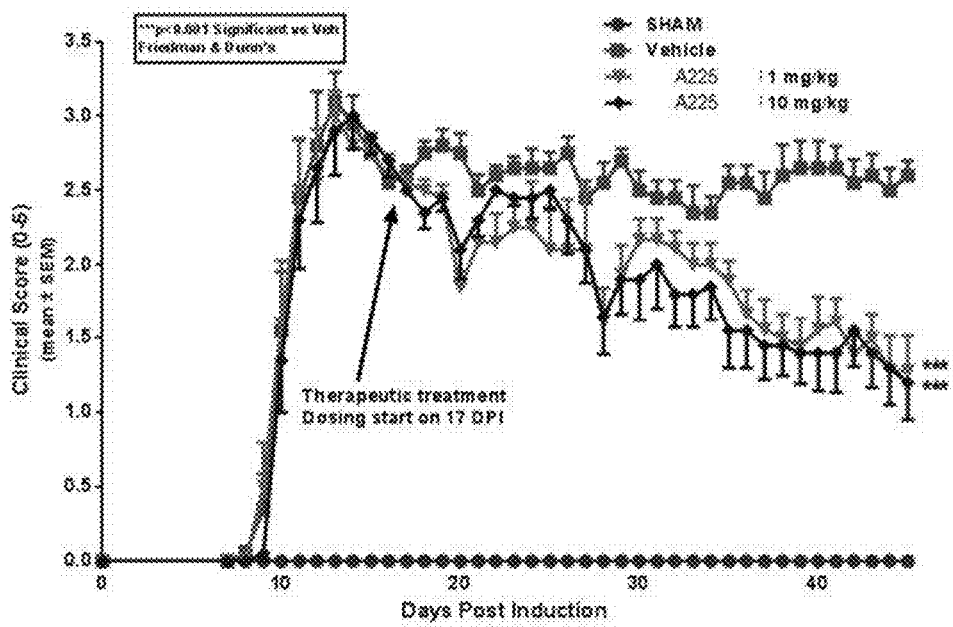
FIG. 18: (a) Therapeutic dosing with Compound (2) reduced disease severity in SJL-EAE; (b) cumulative score.
Figure 18:
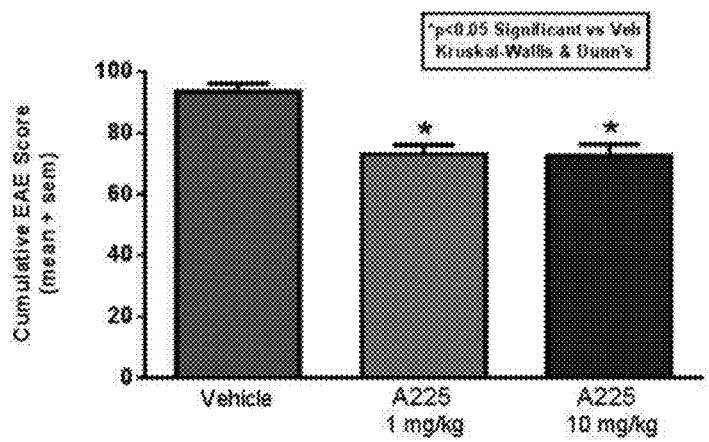
Figure 19:
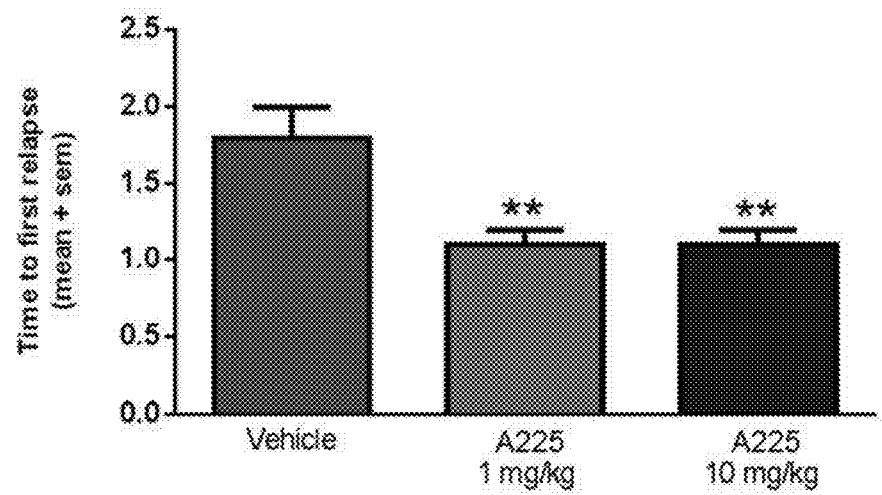
FIG. 19: (a) Therapeutic dosing with Compound (2) reduced the number of relapses; (b) summary.
Figure 20:
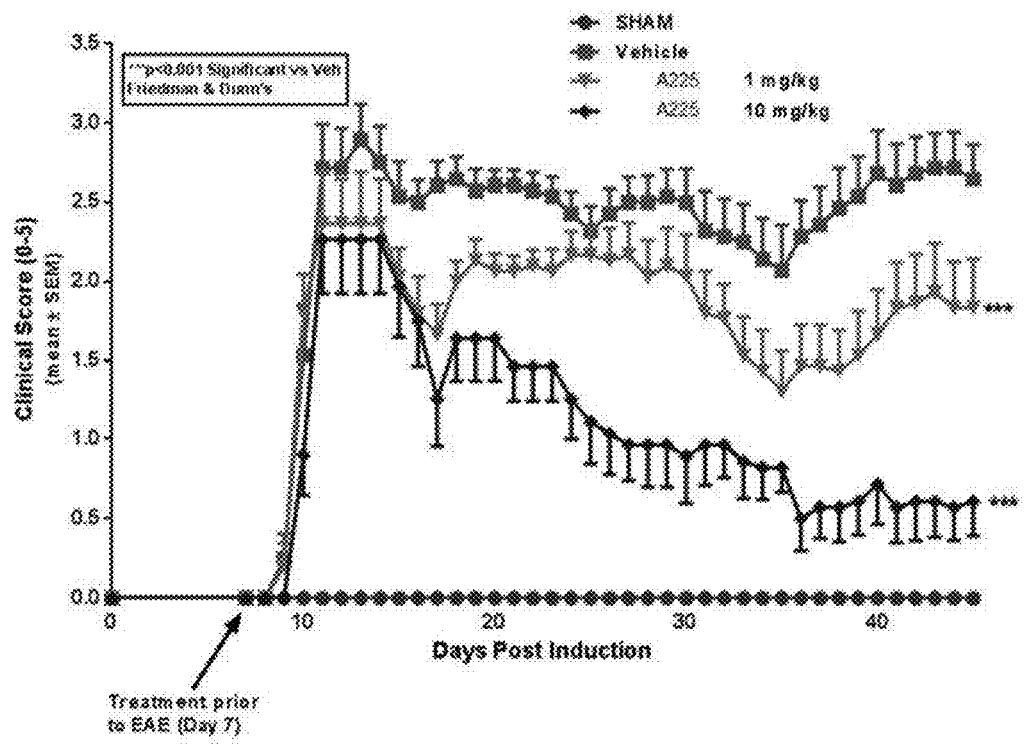
FIG. 20: (a) Semi-therapeutic dosing with Compound (2) reduced disease severity in SJL-EAE; (b) cumulative score.
Figure 20:
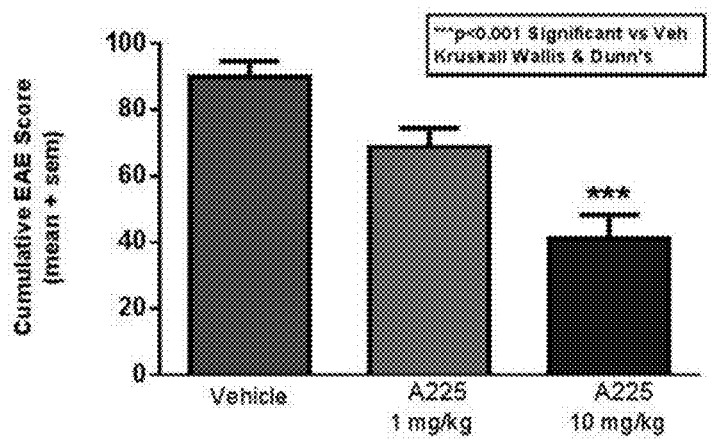
Figure 21:
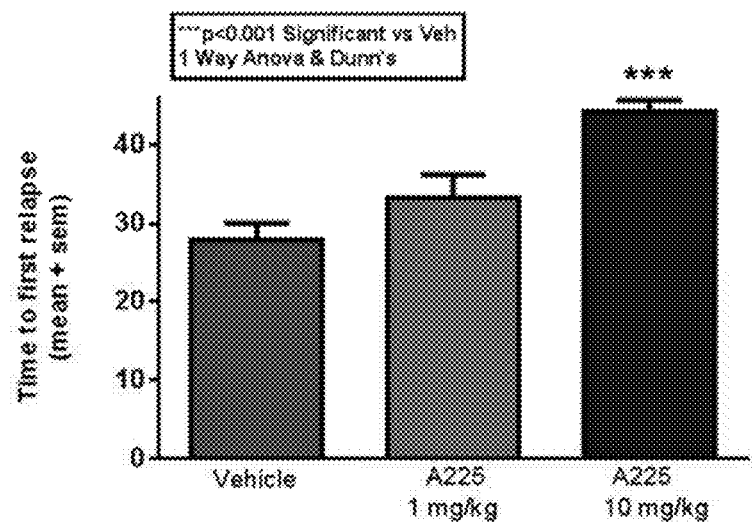
FIG. 21: (a) Therapeutic dosing with Compound (2) reduced the number of relapses; (b) number of relapses; (c) summary.
Figure 21:
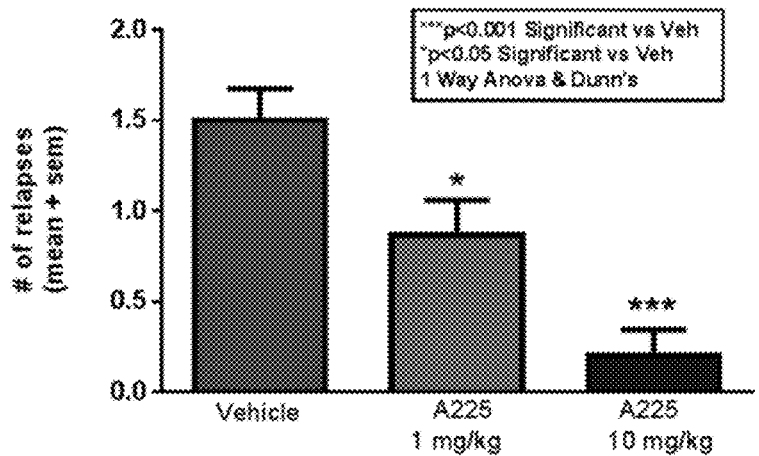

EAE (experimental autoimmune encephalomyelitis) is an animal model of multiple sclerosis (MS). This model reflects certain aspects of the pathology seen in MS including inflammation and demyelination. Compound 2 was administered therapeutically in PLP139-151 induced EAE in female SJL mice. Dosing began on Day 17 post-induction: Vehicle, 1.0 mg/kg and 10 mg/kg PO QD. The endpoint included a clinical score. FIGS. 18-19. Compound 2 was administered therapeutically in PLP139-151 induced EAE in female SJL mice. Dosing began on Day 7 post-induction (before onset of EAE): Vehicle, 1.0 mg/kg and 10 mg/kg PO QD. The endpoint included a clinical score. FIG. 20-21.

Animals: Mice were female SJL mice from Jackson Laboratories. SJL mice were ordered at 8-10 weeks and used between 9-11 weeks. Animals were kept in the convention room of husbandry during the duration of the experiment.

Procedure

1) $PLP_{139-151}$ preparation: $PLP_{139-151}$ peptide solution was prepared at concentration 1-2 mg/mL for in PBS.

2) IFA+MT preparation: OFA supplemented with *M. tuberculosis* $H_{37}RA$ was prepared, as follows: IFA (10 mL/ampoule) was poured into a 50 ml Falcon tube (50 mL for each 100 mg ampoule of desiccated TM $H_{37}RA$). 100 mg of TM $H_{37}RA$ was added into the 50 mL of CFA and homogenize briefly (~1 minute).

3) Emulsion preparation: Equal amounts of IFA/TM and $PLP_{139-151}$ was used for the emulsion. IFA/TM was added into a sterile beaker. The contents were emulsified by adding the $PLP_{139-151}$ solution drop wise with a transfer pipette while homogenizing on low speed. After cooling on ice every few minutes to prevent heating the emulsion (heating peptides might cause denaturation), $PLP_{139-151}$ solution was added and the procedure was repeated until the emulsion had a smooth consistency. The emulsion was homogenized on high-speed for a few seconds (15-30 seconds) to ensure a homogenous emulsion. The stability of the emulsion was tested by extruding a droplet onto the surface of 50 ml of PBS in a reservoir or in a 100 ml beaker. The droplet of emulsion held together without dispersing. The emulsion was kept on ice until use.

4) $PLP_{139-151}$ injection: A 1 mL luerlok syringe was filled with emulsion. A 15 gauge animal feeding needle was added and the feeding needle was dipped into the emulsion and the needle was filled. When needle wass filled, air was expelled from the syringe. Inject 0.2 ml of $PLP_{139-151}$ emulsion in the abdominal flank of each mouse (0.1 ml at 2 sites, close to the lymph nodes) using a 27 gauge needle.

5) PTX preparation: 1 mL of sterile PBS was added to 50 µg PTX (1 vial), and mixed gently. The stock was kept at 4° C. and a fresh solution from the stock was prepared for the injection at 48 h. Before use PTX was diluted with PBS to the desired concentration (0.25-1 ug/mL or 50-100 ng/mouse).

6) PTX injection: SJL mice were injected with 200 ul i.p. using a 25 gauge needle. One injection was done on the same day as $MOG_{35-55}$ injection and repeated again 48 hours later.

7) Body Weight and Clinical Scoring: SJL mice were weighed and clinical score was assessed according to the scoring system at least 3 times/week. At peak of disease (around day 10-15) they were scored every day. The duration of study was up to 10 weeks.

What is claimed is:

1. A method of treating MS, comprising:
   administering to a subject in need thereof a therapeutically effective amount of:
   N-[(1-acryloylpiperidin-4-yl)methyl]-5-(4-phenoxyphenyl)pyrimidine-4,6-diamine (1); 1-(4-(((6-amino-5-(4-phenoxyphenyl)pyrimidin-4-yl)amino)methyl)-4-fluoropiperidin-1-yl)prop-2-en-1-one (2); or a pharmaceutically acceptable salt, a pharmaceutically acceptable tautomer, or a pharmaceutically acceptable stereoisomer thereof.

2. The method according to claim 1, wherein the MS is selected from relapsing MS (RMS), relapsing-remitting MS (RRMS), progressive MS (PMS), secondary-progressive MS (SPMS), primary-progressive MS (PPMS), and progressive-relapsing MS (PRMS).

3. A method of preventing MS, comprising
   administering to a subject in need thereof an effective amount of N-[(1-acryloylpiperidin-4-yl)methyl]-5-(4-phenoxyphenyl)pyrimidine-4,6-diamine (1); or 1-(4-(((6-amino-5-(4-phenoxyphenyl)pyrimidin-4-yl)amino)methyl)-4-fluoropiperidin-1-yl)prop-2-en-1-one (2) or a pharmaceutically acceptable salt, a pharmaceutically acceptable tautomer, or a pharmaceutically acceptable stereoisomer thereof.

4. The method according to claim 3, wherein the MS is selected from relapsing MS (RMS), relapsing-remitting MS (RRMS), progressive MS (PMS), secondary-progressive MS (SPMS), primary-progressive MS (PPMS), and progressive-relapsing MS (PRMS).

* * * * *